(12) United States Patent
Hu et al.

(10) Patent No.: US 7,670,613 B2
(45) Date of Patent: Mar. 2, 2010

(54) ANDROGEN MODULATORS

(75) Inventors: Lain-Yen Hu, Ann Arbor, MI (US); Bruce A. Lefker, Gales Ferry, CT (US); Daniel Y. Du, Milan, MI (US); Yvonne Dorothy Smith, Ypsilanti, MI (US); Huangshu Lei, Waltham, MA (US); William Glen Harter, Chelsea, MI (US); Victoria Leigh Downs, Pinckney, MI (US); Mark L. Boys, Brighton, MI (US); Donna Michele Iula, Ann Arbor, MI (US)

(73) Assignee: Pfizer Inc., New York, NY (US)

( * ) Notice: Subject to any disclaimer, the term of this patent is extended or adjusted under 35 U.S.C. 154(b) by 1274 days.

(21) Appl. No.: 11/175,097

(22) Filed: Jul. 5, 2005

(65) Prior Publication Data

US 2006/0009427 A1 Jan. 12, 2006

Related U.S. Application Data

(60) Provisional application No. 60/586,160, filed on Jul. 8, 2004, provisional application No. 60/598,033, filed on Aug. 2, 2004.

(51) Int. Cl.
*A61K 9/00* (2006.01)

(52) U.S. Cl. .................................... 424/400

(58) Field of Classification Search ........................ None
See application file for complete search history.

(56) References Cited

U.S. PATENT DOCUMENTS

| | | | |
|---|---|---|---|
| 3,535,365 A | 10/1970 | Weinstock | |
| 4,029,493 A | 6/1977 | Theissen | |
| 4,234,595 A | 11/1980 | Kreighbaum et al. | |
| 4,263,223 A | 4/1981 | Pauly | |
| 4,536,321 A | 8/1985 | Sugimori et al. | |
| 4,925,590 A | 5/1990 | Reiffenrath | |
| 4,992,433 A | 2/1991 | Stokbroekx et al. | |
| 5,108,652 A | 4/1992 | Eidenschink et al. | |
| 5,316,755 A | 5/1994 | Illig et al. | |
| 5,847,166 A | 12/1998 | Buchwald et al. | |
| 5,910,493 A | 6/1999 | Golbs et al. | |
| 5,990,142 A | 11/1999 | Carganico et al. | 514/382 |
| 6,011,606 A | 1/2000 | Ohe et al. | |
| 6,124,343 A | 9/2000 | Smith | |
| 2003/0175445 A1 | 9/2003 | Kirsch et al. | |
| 2003/0199427 A1 | 10/2003 | Moye-Sherman | |
| 2003/0229129 A1 | 12/2003 | Kraemer et al. | |
| 2003/0232882 A1* | 12/2003 | Miller et al. | 514/514 |
| 2003/0236304 A1 | 12/2003 | Jolidon | |
| 2004/0006134 A1 | 1/2004 | Labrie | |
| 2005/0182132 A1 | 8/2005 | Hu et al. | |
| 2006/0252796 A1 | 11/2006 | Barrett et al. | |
| 2007/0072936 A1 | 3/2007 | Barrett et al. | |
| 2007/0197641 A1 | 8/2007 | Hu et al. | |
| 2007/0197642 A1 | 8/2007 | Hu et al. | |
| 2007/0207987 A1 | 9/2007 | Barrett et al. | |
| 2008/0064745 A1 | 3/2008 | Lefker et al. | |

FOREIGN PATENT DOCUMENTS

| | | |
|---|---|---|
| CN | 1214048 | 4/1999 |
| DE | 2301541 A1 | 1/1972 |
| DE | 3825170 A1 | 1/1990 |
| DE | 4017019 A1 | 11/1991 |
| DE | 4217928 A1 | 12/1993 |
| EP | 0002309 | 1/1982 |
| EP | 0080371 A | 6/1983 |
| EP | 0119756 | 9/1984 |
| EP | 0193303 | 9/1986 |
| EP | 100172 B1 | 8/1987 |
| EP | 0601977 A | 6/1994 |
| EP | 0684235 A | 11/1995 |
| EP | 0579223 | 10/1996 |
| EP | 1070753 A2 | 1/2001 |
| EP | 1123933 A1 | 8/2001 |
| EP | 070707007 B1 | 12/2001 |
| EP | 1325910 A1 | 7/2003 |
| GB | 2278054 A | 11/1994 |
| JP | 59144747 | 8/1984 |
| JP | 04124183 | 4/1992 |
| JP | 04300877 | 10/1992 |
| JP | 5310616 | 11/1993 |
| JP | 07309850 | 11/1995 |
| WO | WO95/28969 | 11/1995 |
| WO | WO9626921 | 9/1996 |
| WO | WO98/33779 A | 8/1998 |
| WO | WO99/08673 A | 2/1999 |
| WO | WO99/17777 | 4/1999 |
| WO | WO0037430 | 6/2000 |
| WO | WO01/56989 A2 | 8/2001 |
| WO | WO02/06196 A1 | 1/2002 |
| WO | WO02118333 | 3/2002 |
| WO | WO02/057215 A | 7/2002 |
| WO | WO02060896 A | 8/2002 |
| WO | WO02/085860 | 10/2002 |
| WO | WO02/090332 A2 | 11/2002 |
| WO | WO03/065992 A | 8/2003 |
| WO | WO03068217 | 8/2003 |
| WO | WO03068754 | 8/2003 |
| WO | WO03/074473 A | 9/2003 |
| WO | WO03082787 | 10/2003 |
| WO | WO03093243 | 11/2003 |

(Continued)

OTHER PUBLICATIONS

Loeffler L J et al: "Synthesis of Isosteres of P-Amidimophenylpyruvic Acid Inhibitors of Trypsin, Thrombin, and Pancreatic Kallikrein" Mar. 1, 1975 J. Of Med Chem, Amer. Chem. Soc. Wash. pp. 287-292 XP000574801 ISSN: 0022-2623.

(Continued)

*Primary Examiner*—Ardin Marschel
*Assistant Examiner*—Jean Cornet
(74) *Attorney, Agent, or Firm*—Gregg C. Benson; J. Michael Dixon

(57) ABSTRACT

The present invention is directed to a new class of 4-cycloalkoxy benzonitriles and to their use as androgen receptor modulators. Other aspects of the invention are directed to the use of these compounds to decrease excess sebum secretions and to stimulate hair growth.

12 Claims, No Drawings

FOREIGN PATENT DOCUMENTS

| WO | WO2004/018386 A | 3/2004 |
|---|---|---|
| WO | WO2004/018477 A2 | 3/2004 |
| WO | WO2004110994 A1 | 12/2004 |
| WO | WO2005/000794 | 1/2005 |
| WO | WO2005013914 A | 2/2005 |
| WO | WO2005042464 A1 | 5/2005 |
| WO | WO2005/049574 | 6/2005 |
| WO | WO2005080320 A1 | 9/2005 |
| WO | WO2005/100305 A | 10/2005 |
| WO | WO2005/102990 A | 11/2005 |
| WO | WO2005/108361 | 11/2005 |
| WO | WO2005102990 | 11/2005 |
| WO | WO2006006065 | 1/2006 |
| WO | WO2006/018732 A2 | 2/2006 |
| WO | WO2006024942 | 3/2006 |
| WO | WO20006/049952 | 5/2006 |

OTHER PUBLICATIONS

Database Caplus Online Chemical Abstracts Service, Columbus, Ohio US Berg, S,S. et al., chemotherapeutic amidines X. Substituted 4,4'-diamidino-omega.-diphenoxyalkanes and diphenyl ethers XP002333841 retreived from STN Database accession No. 1949:50548 abstract & Journal of the Chemical Society Abstracts, 1949, pp. 642-648.

Database Caplus Online Chemical Abstracts Service, Columbus, Ohio US Kratzl. K. et al: "Chemistry of vanillin and its derivatives X. Amidines imidazolines, and tetrahydropyrimidimediones with quaiacol substituents" XP002333842 Retrieved from STN Database accession No. 1958:65868 abstract & Monatshefte Fuer Chemie, 88, 1957, pp. 1056-1063.

Database Caplus Online Chemical Abstracts Service, Columbus, Ohio US Davis, M.: "Search for chemotherapeutic amidines. XV. 2-Methoxy and 2-hydroxy derivatives of 1,5-bis(p-amidinophenoxy) pentane" XP002333843 retrieved from STN Database accession No. 1958:82447 abstract & Journal of the Chemical Society, Abstracts, 1958, pp. 907-908.

Data Base CA Online Chemical Abstracts Service, Columbus, Ohio, US; Ferroni, R. et al., "Aromatic tetra-amidines: synthesis of halo-derivatives and their antiproteolytic activity" XP002333844 retrieved from STN Database accession No. 1985:91904 abstract & Farmaco, Edizione Scientifca, vol. 39, No. 11, 1984, pp. 901-909.

Data Base Caplus Online Chemical Abstracts Service. Columbus, Ohio US Leznoff, Clifford C et al.; "Metallophthalocyanine dimers incorporating five-atom covalent bridges" XP002333845 retrieved from STN Databse accession No. 1985:447150 abstract & Canadian Journal of Chemistry vol. 63 No. 3, 1985, pp. 623-631.

Data Base Caplus Online Chemical Abstracts Service, Columbus, Ohio US Woehrle, Dieter et al: "Polymeric phthalocyanines and their precursors. 15. Syntheses of alkyllenedioxy-bridged polyoneric phthalocyanines and their absorption capacities for organic solvents in comparison to other phthalocyanines" XP002333846 retreieved from STN Database accession No. 1988 493734 abstract & Makromolekulare Chemie, vol. 189, No. 6, 1988, pp. 1229-1238.

Geratz, J.D. et al: "Diamidino-alpha.. omega.-diphenoxyalkane s. Structure-activity relations for the inhibition of thrombin, pancreatic kallikrein, and trypsin" Journal of Medicinal Chemistry, vol. 16, No. 9, 1973, pp. 970-975, XP002333840 table VI, compounds 27-30, 32-34, 37.

Database Caplus, Online Chemical Abstracts Service, Columbus, Ohio US. Csokai, Viktor et al: " Microwave-assisted synthesis of phtalonitriles and phthalocyanines"XP002333847 retreived from STN Database accession No. 2003:416216 abstract & Synthetic Communications, vol. 33, No. 10, 2003, pp. 1615-1621.

Database Caplus, Online Chemical Abstracts Service, Columbus, Ohio. US: Eastmond, G.C. et al: "Polyimides with main-chain ethylene oxide units:synthesis and properties" retreived from STN Database accession No. 2002:264464 abstract & Polymer, vol. 43, No. 12. 2002, pp. 3455-3468.

Database Caplus, Online Chemical Abstracts Service, Columbus, Ohio. US; Zhang, Yisheng et al: "Tetranuclear Hexanuclear. and Octanuclear Copper (II) Complexes of a Series of Novel Dendritic Poly(phthalazine) Ligands" XP002333849 retrieved from STN Database accession No. 1995:875232 abstract & Inorganic Chemistry, vol. 34, No. 23, 1995, pp. 5870-5877.

Database Caplus, Online Chemical Abstracts Service, Columbus, Ohio, US: Kobayashi. Nagao et al: "Optically active phthalocyanines and their circular dichroism" XP002333850 retreived from STN Database accession No. 1993:652129 abstract & Journal of the American Chemical Society. vol. 115, No. 23, 1993. pp. 10994-10995.

Database Caplus, Online Chemical Abstracts Service. Columbus, Ohio, US; Keller, Teddy M. et al: "Synthesis of phthalonitriles by nitro displacement" XP002333851 retrieved from STN Database accession No. 1981:442589 abstract & Synthesis, No. 8. 1980, p. 613.

Database Caplus, Online Chemical Abstracts Service. Columbus, Ohio. US: Dann, Otto et al.: "Syntheses of biscationi, trypanocidal 1-benzofuran compounds" XP002333852 retrieved from STN Database accession No. 1983:53580 abstract & Liebigs Annalen Der Chemie, No. 10, 1982, p. 1836.

FR 2397387 A (Laboratoires Serobiologiques SA) Feb. 9, 1979 p. 4. line 4-line 10; claim 12; example IU (US4263223 US equivalent).

Database VA Online Chemical Abstracts Service. Columbus Ohio US; Chang, Chih-Shiang et al.: "Design and synthesis of 1,2, 4-oxadiazole derivatives as non-steroidal 5 alpha -reductase inhibitors" XP002419614 retreived from STN & Journal of the Chinese Chemical Society (Taipei, Taiwan), 49(1), 83-89 CODEN: JCCTAC, ISSN: 000904536, 2002.

Database VA Online Chemical Abstracts Service, Columbus Ohio US; Ashley, J.N. et al.: "Chemotherapeutic Comparison of the trypanocidal action of some aromatic diamidines" XP002419615 retrieved from STN Database accession No. 1942:22799 abstract & Journal of the Chemical Society 103-16 CODEN: JCSOA9; ISSN: 0368-1769, 1942.

Database VA Online Chemical Abstracts Service. Columbus Ohio US; DOI, Fuminao et al.: "Synthesis of chroman derivatives by the ring expansion reaction of spirodienones, and an assessment of their plant growth inhibition" XP002419616 retrived from STN Database accession No. 2004:1127989 abstract & Bulletin of the Chemical Society of Japan, 77(12), 2257-2263, CODEN : BCSJA8; ISSN: 0009-2673.

Palucki, M et al., "Palladium-catalyzed intermolecularcarbon-oxygen bond formation; A new synthesis of aryl ethers", J. Am. Chem. Soc., 1997, vol. 119, nr. 14, pp. 3395-3396.

Database CA [Online] Chemical Abstracts Service, Columbus, Ohio, US; Yasuda, Kosuke et al: "Preparation of aliphatic nitrogenous five-membered ring compounds as dipeptidyl peptidase IV inhibitors" XP002350473 retrived from STN Database accession No. 136:325560.

Database CA [Online] Chemical Abstracts Service, Columbus, Ohio, US; Chaki, Hisaaki et al: "Preparation and formulation of alkylsulfonylbiphenyl and aminosulfonylbiphenyl derivatives as selective COX-2 inhibitors" XP002350472 retrieved from STN Database accession No. 125:300608.

Kuwabe, S., et al., "Palladium Catlalized Intramolecular C-O Bond Formation", J. Am. Chem Soc., vol. 123, pp. 12202-12206 (2001).

Patent Abstracts of Japan vol. 013, No. 021 (C-560), Jan. 18, 1989 & JP 63227502A (SDS Biotech KK), Sep. 21, 1988.

Reiling B A et al: "Effect of prenatal androgenization on performance, lactation, carcass, and sensory traits of heifers in a single-calf heifer system" Journal of Animal Science, vol. 73, No. 4, 1995, pp. 986-992, XP0088065209 ISSN: 0021-8812.

Heitzman R J: "The effectiveness of anabolic agents in increasing rate of growth in farm animals; report on experiments in cattle." Environmental Quality and Safety. Supplement, 1976, No. 5, 1976, pp. 89-98, XP008065222 ISSN: 0340-4714.

Botzki, Salmen: "Structure based design . . . " Cominatorial Science, vol. 24, No. 4, 2005, pp. 458-469, XP008065218.

Alexandre Alexakis et al., Enantioselective Nucleophilie Opening for meso Epoxides by Organolithium Reagents, Synlett Oct. 1998, pp. 1165-1167.

Shankar M. Shingh et al., Androgen Receptor Antagonists (Antiandrogens): Structure-Activity Relationships, Current Medicinal Chemistry, 2000, 7, 211-247.

Micropatent English Abstract of Japanese Patent (JP2001-247411).

Qian, et al., *J. Chem. Tech. Biotechnol.*, vol. 67, pp. 124-130 (1996).

Wagner, et al., *Tetrahedron Letters*, vol. 43, pp. 3569-3571 (2002).

Bohl, Casey E., et al., Structural basis for antagonism and resistance of bicalutamide in prostate cancer, PNAS, Apr. 26, 2005, vol. 102, No. 17 pp. 6201-6206.

* cited by examiner

ANDROGEN MODULATORS

This application claims priority to U.S. Provisional Applications Ser. Nos. 60/586,160, filed Jul. 8, 2004 and 60/598,033, filed Aug. 2, 2004.

The entire disclosure of parent application filed is fully incorporated herein by reference thereto.

FIELD OF THE INVENTION

The present invention is directed to a new class of 4-cycloalkoxy benzonitriles and to their use as androgen receptor modulators. Other aspects of the invention are directed to the use of these compounds to decrease sebum secretion and to stimulate hair growth.

BACKGROUND OF THE INVENTION

Alopecia, or balding, is a common problem which medical science has yet to alleviate. While androgens are associated with balding, the physiological mechanism by which this hair loss occurs is not known. However, it is known that hair growth is altered in individuals afflicted with alopecia.

Hair does not grow continuously but undergoes cycles of activity involving periods of growth, rest, and shedding. The human scalp typically contains from 100,000 to 350,000 hair fibers or shafts, which undergo metamorphosis in three distinct stages:

(a) during the growth phase (anagen) the follicle (i.e. the hair root) penetrates deep into the dermis with the cells of the follicle dividing rapidly and differentiating in the process of synthesizing keratin, the predominant component of hair. In non-balding humans, this growth phase lasts from one to five years;

(b) the transitional phase (catagen) is marked by the cessation of mitosis and lasts from two to three weeks; and (c) the resting phase (telogen) in which the hair is retained within the scalp for up to 12 weeks, until it is displaced by new follicular growth from the scalp below.

In humans, this growth cycle is not synchronized. An individual will have thousands of follicles in each of these three phases. However, most of the hair follicles will be in the anagen phase. In healthy young adults, the anagen to telogen ratio can be as high as 9 to 1. In individuals with alopecia, this ratio is reduced to as low as 2:1.

Androgenetic alopecia arises from activation of an inherited sensitivity to circulating androgenic hormones. It is the most common type of alopecia. It affects both men (50%) and women (30%), primarily of Caucasian origin. Gradual changes in the width and length of the hair shaft are experienced over time and with increasing age, prematurely in some. Terminal hair is gradually converted to short, wispy, colorless vellus hair. As a consequence, men in there 20's and women in their 30's and 40's begin to notice their hair becoming finer and shorter. In males, most of the hair loss occurs at the crown of the head. Females experience a thinning over their entire scalp. As discussed above, the anagen to telogen ratio is reduced significantly, resulting in less hair growth.

Minoxidil, a potassium channel opener, promotes hair growth. Minoxidil is available commercially in the United States under the trademark, Rogaine®. While the exact mechanism of action of minoxidil is unknown, its impact on the hair growth cycle is well documented. Minoxidil promotes the growth of the hair follicle and increase the period of time that the hair follicle is in the anagen phase (i.e., increases the anagen to telogen ratio).

While minoxidil promotes hair growth, the cosmetic efficacy of this growth can vary widely. For example, Roenigk reported the results of a clinical trial involving 83 males who used a topical solution of 3% minoxidil for a period of 19 months. Hair growth occurred in 55% of the subjects. However, only 20% of the subjects considered the growth to be cosmetically relevant. (*Clin. Res.*, 33, No. 4, 914A, 1985). Tosti reported cosmetically acceptable re-growth in 18.1% of his subjects. (*Dermatologica*, 173, No. 3, 136-138, 1986). Thus, the need exists in the art for compounds having the ability produce higher rates of cosmetically acceptable hair growth in patients with alopecia.

SUMMARY OF THE INVENTION

In accordance with the present invention, a new class of 4-cycloalkoxy benzonitriles has been discovered. These compounds, their salts, solvates, and prodrugs thereof, may be represented by Formula I below:

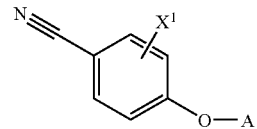

in which;

a) $X^1$ is represented by halogen, cyano, $C_1$-$C_6$ alkoxy, haloalkoxy, or haloalkyl and, b) A is represented by a cycloalkyl or cyloalkenyl ring as depicted below:

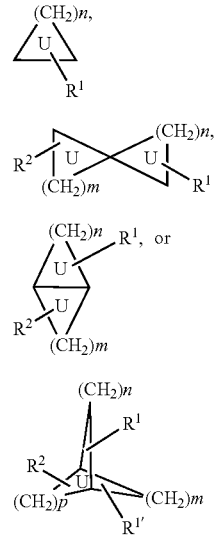

c) n, m and p are each independently represented by an integer from 1 to 8, d) the symbol U indicates the optional presence of one, or more, carbon-carbon double bonds, e) $R^1$, $R^{1'}$ and $R^2$ are each independently represented by a substituent selected from the group consisting of:
  i) hydrogen,
  ii) halogen,
  iii) cyano, iv) hydroxy,
v) $(C_1\text{-}C_{12})$alkyl, optionally substituted,
vi) $(C_2\text{-}C_{12})$alkenyl, optionally substituted,
vii) $(C_2\text{-}C_{12})$alkynyl, optionally substituted,
viii) $(C_3\text{-}C_{10})$cycloalkyl, optionally substituted,
ix) $(C_3\text{-}C_{10})$ cycloalkyl$(C_1\text{-}C_6)$alkyl, in which the alkyl and cycloalkyl moieties may each be optionally substituted,
x) $(C_6\text{-}C_{10})$ary, optionally substituted,
xi) $(C_6\text{-}C_{10})$aryl $(C_1\text{-}C_6)$alkyl, in which the alkyl and aryl moieties may each be optionally substituted,
xii) $(CH_2)_z\text{—}SR^3$,
xiii) $(CH_2)_z\text{—}OR^3$,
xiv) $(CH_2)_z\text{—}NR^3R^4$,
xv) $(CH_2)_z\text{—}COOR^3$,
xvi) $(CH_2)_z\text{—}CONR^3$,
xvii) $(CH_2)_z\text{—}NCOR^3$, and
xviii) $(CH_2)_zOCOR^3$;

f) z is represented by an integer from 0 to 6, g) $R^3$ is represented by a substituent selected from the group consisting of hydrogen, $(C_1\text{-}C_{12})$alkyl, $(C_2\text{-}C_{12})$alkenyl, $(C_2\text{-}C_{12})$alkynyl, optionally substituted $(C_6\text{-}C_{10})$ary, and $(C_6\text{-}C_{10})$aryl $(C_1\text{-}C_6)$alkyl, in which the alkyl and aryl moieties may each be optionally substituted and;

f) $R^4$ is represented by a substituent selected from the group consisting of hydrogen, and $(C_1\text{-}C_{12})$alkyl.

The compounds of Formula I are androgen receptor modulators. The compounds have affinity for the androgen receptor and will cause a biological effect by binding to the receptor. Typically, the compounds will act as antagonists. In selected embodiments they will act as partial agonists, full agonists, or tissue selective agonists. As androgen receptor modulators, the compounds can be used to treat, or alleviate, conditions associated with inappropriate activation of the androgen receptor. Examples of such conditions for antagonists include, but are not limited to, acne, excess sebum secretion, androgenic alopecia, hormone dependant cancers such as prostrate cancer, and hirsutism. Those compounds that are partial agonists, or full agonists, can be used to treat osteoporosis, hypogonadism, anemia, or to stimulate increases in muscle mass, especially in wasting diseases.

The invention is also directed to pharmaceutical compositions containing at least one of the compounds, in an amount effective to modulate activation of the androgen receptor. In a further embodiment, the invention is directed to an article of manufacture containing at least one of the compounds packaged for retail distribution, in association with instructions advising the consumer on how to use the compound to alleviate a condition associated with inappropriate activation of the androgen receptor. An additional embodiment is directed to the use of a compound as a diagnostic agent to detect inappropriate activation of the androgen receptor.

In a further embodiment, the compounds are used topically to induce and/or stimulate hair growth and/or to slow down hair loss. The compounds may also be used topically in the treatment of excess sebum and/or of acne.

In a further embodiment the compounds can be used in livestock such as cattle, pigs, chickens, fish, etc. The compounds will increase the growth rate, and enhance the lean meat to fat ratio in the animals, and improve feed efficiency.

DETAILED DESCRIPTION OF THE INVENTION

The headings within this document are only being utilized expedite its review by the reader. They should not be construed as limiting the invention or claims in any manner.

Definitions and Exemplification

As used throughout this application, including the claims, the following terms have the meanings defined below, unless specifically indicated otherwise. The plural and singular should be treated as interchangeable, other than the indication of number:

a. "halogen" refers to a chlorine, fluorine or bromine atom.

b. "$C_1\text{-}C_6$ alky" refers to a branched or straight chained alkyl group containing from 1 to 6 carbon atoms, such as methyl, ethyl, n-propyl, isopropyl, n-butyl, isobutyl, pentyl, etc.

c. "$C_1\text{-}C_6$ alkyl, optionally substituted" refers to a branched or straight chained alkyl group containing from 1 to 6 carbon atoms, such as methyl, ethyl, n-propyl, isopropyl, n-butyl, isobutyl, pentyl, etc. Such an alkyl group may be optionally substituted, in which up to 6 hydrogen atoms are replaced by a substituent selected from the group consisting of halogen, haloalkyl, hydroxy, thiol, cyano, and $NR^3R^4$ in which $R^3$ and $R^4$ are as defined above.

d. "$C_1\text{-}C_{12}$ alkyl, optionally substituted" refers to a branched or straight chained alkyl group containing from 1 to 12 carbon atoms, such as methyl, ethyl, n-propyl, isopropyl, n-butyl, isobutyl, hexyl, octyl, decyl, etc. Such an alkyl group may be optionally substituted, in which up to 8 hydrogen atoms are replaced by a substituent selected from the group consisting of halogen, haloalkyl, hydroxy, thiol, cyano, and $NR^3R^4$, in which $R^3$ and $R^4$ are as defined above.

e. "$C_2\text{-}C_{12}$ alkenyl optionally substituted" refers to a straight-chain or branched-chain hydrocarbon radical containing from 2 to 12 carbon atoms and 1, or more, carbon-carbon double bonds. Examples of alkenyl radicals include ethenyl, propenyl, 1,4-butadienyl, 1-hexenyl, 1,3-octadienyl and the like. Such an alkenyl group may be optionally substituted, in which up to 8 hydrogen atoms are replaced by a substituent selected from the group consisting of halogen, haloalkyl, hydroxy, thiol, cyano, and $NR^3 R^4$, in which $R^3$ and $R^4$ are as defined above.

f. "$C_2\text{-}C_{12}$ alkynyl optionally substituted" refers to a straight-chain or branched-chain hydrocarbon radical containing from 2 to 12 carbon atoms and having 1, or more, carbon-carbon triple bonds. Examples of alkynyl radicals include ethynyl, propynyl, butynyl, octynyl, and the like. Such an alkynyl group may be optionally substituted, in which up to 8 hydrogen atoms are replaced by a substituent selected from the group consisting of halogen, hydroxy, haloalkyl, thiol, cyano, and —$NR^3R^4$, in which $R^3$ and $R^4$ are as defined above.

g. "haloalkyl" refers to a branched or straight chained alkyl group containing from 1 to 6 carbon atoms, in which at least one hydrogen atom is replaced with a halogen (i.e. $C_1\text{-}C_6$ haloalkyl). Examples of suitable haloalkyl's include chloromethyl, difluoromethyl, trifluoromethyl, 1-fluoro-2-chloro-ethyl, 5-fluoro-hexyl, 3-difluoro-isopropyl, 3-chloro-isobutyl, etc.

h. "$(C_1\text{-}C_2)$alkyl substituted with one or more halogen atoms" refers to a straight chained alkyl group containing 1 or 2 carbon atoms, i.e., methyl or ethyl in which at least one hydrogen atom is replaced with a halogen (i.e. for example trifluromethyl, dichloromethyl, etc.).

i. "$(C_1\text{-}C_2)$alkoxy substituted with one or more halogen atoms" refers to a straight chained alkoxy group containing 1 or 2 carbon atoms, i.e., methoxy or ethoxy in which at least one hydrogen atom is replaced with a halogen (i.e. for example trifluoromethoxy, difluromethoxy, etc.)

j. "$C_1$-$C_6$ alkoxy" refers to a straight or branched chain alkoxy group containing from 1 to 6 carbon atoms, such as methoxy, ethoxy, n-propoxy, isopropoxy, n-butoxy, isobutoxy, pentoxy, etc.

k. "haloalkoxy" refers to a branched or straight chained alkoxy group containing from 1 to 6 carbon atoms, in which at least one hydrogen atom is replaced with a halogen (i.e. $C_1$-$C_6$ haloalkoxy). Examples of suitable haloalkoxy's include chloromethoxy, difluoromethoxy, trifluoromethoxy, 1-fluro-2-chloro-ethoxy, 5-fluoro-hexoxy, 3-difluro-isopropoxy, 3-chloro-isobutoxy, etc.

l. "($C_6$-$C_{10}$)aryl" optionally substituted means a cyclic, aromatic hydrocarbon containing from 6 to 10 carbon atoms. Examples of aryl groups include phenyl, naphthyl and biphenyl. Such an aryl moiety may be optionally substituted with up to 4 non-hydrogen substituents, each substituent is independently selected from the group consisting of halogen, cyano, hydroxy, ($C_1$-$C_6$) alkyl, ($C_1$-$C_6$)alkoxy, ($C_1$-$C_2$)alkyl substituted with one or more halogens, ($C_1$-$C_2$)alkoxy substituted with one or more halogens, $SR^5$ and $NR^5R^6$. $R^5$ and $R^6$ are each independently represented by $C_1$-$C_6$ alkyl or hydrogen. These substituents may be the same or different and may be located at any position of the ring, that is chemically permissible.

m. "($C_3$-$C_{10}$) cycloalkyl" optionally substituted refers to a saturated or partially saturated monocyclic, bicyclic or tricyclic alkyl radical wherein each cyclic moiety has 3 to 10 carbon atoms. Examples of cycloalkyl radicals include cyclopropyl, cyclobutyl, cyclopentyl, cyclohexyl, cyclooctyl, and the like. Such a cycloalkyl group may be optionally substituted, in which up to 4 hydrogen atoms are replaced by a substituent selected from the group consisting of halogen, cyano, hydroxy, ($C_1$-$C_6$) alkyl, ($C_1$-$C_6$)alkoxy, ($C_1$-$C_2$)alkyl substituted with one or more halogens, ($C_1$-$C_2$)alkoxy substituted with one or more halogens, $SR^5$, and $NR^5R^6$, in which $R^5$ and $R^6$ are as defined above.

n. "androgen" refers to testosterone and its precursors and metabolites, and 5-alpha reduced androgens, including but not limited to dihydrotestosterone. Androgen refers to androgens from the testis, adrenal gland, and ovaries, as well as all forms of natural, synthetic and substituted or modified androgens.

o. "pharmaceutically acceptable" means suitable for use in mammals.

p. "salts" is intended to refer pharmaceutically acceptable salts and to salts suitable for use in industrial processes, such as the preparation of the compound.

q. "pharmaceutically acceptable salts" is intended to refer to either pharmaceutically acceptable acid addition salts" or "pharmaceutically acceptable basic addition salts" depending upon actual structure of the compound.

r. "pharmaceutically acceptable acid addition salts" is intended to apply to any non-toxic organic or inorganic acid addition salt of the base compounds represented by Formula I or any of its intermediates. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids, which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, p-toluenesulfonic acid, and sulfonic acids such as methane sulfonic acid and 2-hydroxyethane sulfonic acid. Such salts can exist in either a hydrated or substantially anhydrous form. In general, the acid addition salts of these compounds are soluble in water and various hydrophilic organic solvents, and which in comparison to their free base forms, generally demonstrate higher melting points.

s. "pharmaceutically acceptable basic addition salts" is intended to apply to any non-toxic organic or inorganic basic addition salts of the compounds represented by Formula I, or any of its intermediates. Illustrative bases which form suitable salts include alkali metal or alkaline-earth metal hydroxides such as sodium, potassium, calcium, magnesium, or barium hydroxides; ammonia, and aliphatic, alicyclic, or aromatic organic amines such as methylamine, dimethylamine, trimethylamine, and picoline.

t. "prodrug" refers to compounds that are rapidly transformed in vivo to yield the parent compound of the above formulas, for example, by hydrolysis in blood. A thorough discussion is provided in T. Higuchi and V. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are incorporated herein by reference.

u. "compound of Formula I", "compounds of the invention", and "compounds" are used interchangeably throughout the application and should be treated as synonoms.

v. "patient" refers to warm blooded animals such as, for example, guinea pigs, mice, rats, gerbils, cats, rabbits, dogs, monkeys, chimpanzees, stump tail macques, and humans.

w. "treat" refers to the ability of the compounds to either relieve, alleviate, or slow the progression of the patient's disease (or condition) or any tissue damage associated with the disease.

x. "livestock" refers to animals suitable for human meat consumption. Examples include pigs, cattle, chickens, fish, turkeys, rabbits, etc.

y. "isomer" means "stereoisomer" and "geometric isomer" as defined below.

z. "stereoisomer" means compounds that possess one or more chiral centers and each center may exist in the R or S configuration. Stereoisomers includes all diastereomeric, enantiomeric and epimeric forms as well as racemates and mixtures thereof.

aa. "geometric isomer" means compounds that may exist in cis, trans, anti, entgegen (E), and zusammen (Z) forms as well as mixtures thereof.

Certain of the compounds of the formula (I) may exist as geometric isomers. The compounds of the formula (I) may possess one or more asymmetric centers, thus existing as two, or more, stereoisomeric forms. The present invention includes all the individual stereoisomers and geometric isomers of the compounds of formula (I) and mixtures thereof.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention. The compounds may also exist in one or more crystalline states, i.e. polymorphs, or they may exist as amorphous solids. All such forms are encompassed by the claims.

All of the compounds of Formula I contain a phenyl ring. To further exemplify the invention, the numbering system for this ring and its substitution pattern is shown below:

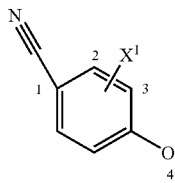

Position 1 of this phenyl ring is substituted with a cyano moiety as depicted above. Position 4 is substituted with an oxygen atom forming an ether moiety. The phenyl ring will be further substituted, as depicted by $X^1$, at position 2 or 3 with a halogen atom, a cyano group, a $(C_1-C_6)$ alkoxy group, a haloalkoxy moiety or a haloalkyl moiety. Typically, it will be a halogen or haloalkyl moiety located at the 2-position. More typically it will be trifluoromethyl located at the 2-position of the phenyl ring.

All of the compounds of Formula I contain a cycloalkyl or cycloalkenyl moiety, as represented by A in Formula I (hereinafter collectively "cycloalkyl"). This cycloalkyl moiety may contain a single ring as depicted by ring (i). This ring may contain from 3 to 10 carbon atoms (i.e. cyclopropyl, cyclobutyl, cyclopentyl, cyclohexyl, cycloheptyl, cyclooctyl, cyclononanyl or cyclodecyl). Up to 6 hydrogen atoms of this cycloalkyl moiety may be replaced with one of the substituents listed above for $R^1$, $R^{1'}$ or $R^2$ (if chemically permissible). These substituents may be the same or different. They may be located on the same carbon atom or different carbon atoms.

One, or more, carbon-carbon double bonds may be introduced into this cycloalkyl ring thereby transforming it into a cycloalkenyl ring. The number of permissible double bonds will vary with the size of the ring and will never be in a quantity sufficient to introduce aromaticity into the ring. For example, a cyclohexyl ring may optionally contain one or two carbon-carbon double bonds; whereas a cyclopentyl ring may only contain 1 carbon-carbon double bond. The double bonds may be located on any position of the ring, (that is chemically permissible).

A may also represent one of the bicyclic rings depicted above. The rings may be spiro (sharing one common atom, see ring ii), fused (sharing one common bond, see ring iii) or bridged (see ring iv). Each individual ring may contain from 3 to 10 carbon atoms (i.e. cyclopropyl thru cyclodecyl as described above). The number of carbon atoms in each ring may be the same or may differ. Up to 6 hydrogen atoms of each individual ring may be replaced with one of the substituents listed above for $R^1$, $R^{1'}$ and $R^2$ (if chemically permissible) as described immediately above. Each of these rings may contain one, or more carbon-carbon double bonds as described immediately above.

More specific embodiments of the invention include compounds of Formula I in which:

i) $X^1$ is chloro or trifluoromethyl and is located at the 2-position of the phenyl ring, and A is as defined above;

ii) $X^1$ is chloro or trifluoromethyl and is located at the 2-position of the phenyl ring, A is represented by ring (i), n and $R^1$ are as defined above;

iii) $X^1$ is chloro or trifluoromethyl and is located at the 2-position of the phenyl ring, A is cyclobutyl, cyclopentyl or cyclohexyl, and $R^1$ is as defined above.

iv) $X^1$ is chloro or trifluoromethyl and is located at the 2-position of the phenyl ring, A is represented by cyclopentyl or cyclohexyl, and $R^1$ is a substituent selected from the group consisting of hydrogen, cyano, $C_1-C_{12}$alkyl, $C_1-C_{1-2}$ alkenyl, hydroxy, and $C_1-C_6$ alkoxy.

v) $X^1$ is chloro and is located at the 2-position of the phenyl ring, A is represented by cyclobutyl, cyclopentyl or cyclohexyl, and $R^1$ is a substituent selected from the group consisting of hydrogen, hydroxy, cyano, methyl, ethyl, and methoxy.

vi) $X^1$ is methoxy and is located at the 2-position of the phenyl ring, A is represented by cyclobutyl, cyclopentyl or cyclohexyl, and $R^1$ is a substituent selected from the group consisting of hydrogen, hydroxy, cyano, methyl, ethyl, and methoxy.

vii) $X^1$ is trifluoromethyl and is located at the 2-position of the phenyl ring, A is represented by cyclobutyl, cyclopentyl or cyclohexyl, and $R^1$ is a substituent selected from the group consiting of hydrogen, hydroxy, cyano, methyl, ethyl, and methoxy.

More specific examples of compounds represented by formula I include:

i) 4-(5-hydroxy-5-methyl-bicyclo[2.2.1]-hept-2-yloxy)-2-trifluoromethyl-benzonitrile;

ii) 4-(2-methyl-cyclopentyloxy)-2-trifluoromethyl-benzonitrile;

iii) 4-cyclohexyloxy-2-trifluoromethyl-benzonitrile;

iv) 4-(1-allyl-cyclohexyloxy)-2-trifluoromethyl-benzonitrile;

v) 4-cycloheptyloxy-2-trifluoromethyl-benzonitrile;

vi) 4-(2,3-dimethyl-cyclohexyloxy)-2-trifluoromethyl-benzonitrile;

vii) 4-(2-ethyl-cyclohexyloxy)-2-trifluoromethyl-benzonitrile;

viii) 4-(2-methyl-cyclohexyloxy)-2-trifluoromethyl-benzonitrile;

ix) 4-cyclopentyloxy-2-trifluoromethyl-benzonitrile;

x) 4-(2,6-dimethyl-cyclohexyloxy)-2-trifluoromethyl-benzonitrile;

xi) 4-(5-isopropenyl-2-methylcyclohexyloxy)-2-trifluoromethyl-benzonitrile;

xii) 4-(5-isopropenyl-2-methyl-cyclohexyloxy)-2-trifluoromethyl-benzonitrile;

xiii) 4-(2-cyano-cyclohexyloxy)-2-trifluoromethyl-benzonitrile;

xiv) 4-(3-methoxy-cyclohexyloxy)-2-trifluoromethyl-benzonitrile;

xv) 4-(3-methyl-cyclohexyloxy)-2-trifluoromethyl-benzonitrile;

xvi) 4-cyclobutyloxy)-2-trifluoromethyl-benzonitrile;

xvii) 2-chloro-4-(5-hydroxy-5-methyl-bicyclo[2.2.1]-hept-2-yloxy)-benzonitrile;

xviii) 2-chloro-4-(2,3-dimethyl-cyclohexyloxy)-benzonitrile;

xix) 4-(1-butyl-cyclopentyloxy)-2-chloro-benzonitrile;

xx) 2-chloro-4-(2-ethyl-cyclohexyloxy)-benzonitrile;

xxi) 2-chloro-4-(3-methyl-cyclopentyloxy)-benzonitrile;

xxii) 4-bicyclo[2.2.1]-hept-2-yloxy)-2-chloro-benzonitrile;

xxiii) 2-chloro-4-(3-hydroxy-cyclohexyloxy)-benzonitrile;

xxiv) 2-chloro-4-(2-ethyl-cyclohexyloxy)-benzonitrile;

xxv) 2-chloro-4-(2-methyl-cyclohexyloxy)-benzonitrile;

xxvi) 2-chloro-4-(2-phenyl-cyclohexyloxy)-benzonitrile;
xxvii) 2-chloro-4-(4-methyl-cyclohexyloxy)-benzonitrile;
xxviii) 2-chloro-4-(2-methoxy-cyclopentyloxy)-benzonitrile;
xxix) 2-chloro-4-(2-methoxy-cyclohexyloxy)-benzonitrile;
xxx) 4-(2-allyloxy-cyclopentyloxy)-2-chloro-benzonitrile;
xxxi) 3-chloro-4-(2-methoxy-cyclohexyloxy)-benzonitrile;
xxxii) 3-chloro-4-(3,3,5,5-tetramethyl-cyclohexyl)-benzonitrile;
xxxiii) 3-chloro-4-cycloheptyloxy-benzonitrile;
xxxiv) 2-chloro-4-cyclohexyloxy-benzonitrile;
xxxv) 2-chloro-4-cyclopentyloxy-benzonitrile;
xxxvi) 2-chloro-4-(2-isopropyl-5-methyl-cyclohexyloxy)-benzonitrile;
xxxvii) 2-chloro-4-(3-methyl-cyclohexyloxy)-benzonitrile;
xxxviii) 2-chloro-4-(5-isopropenyl-2-methylcyclohexyloxy)-benzonitrile;
xxxix) 2-chloro-4-(2-cyano-cyclohexyloxy)-benzonitrile;
xl) 2-chloro-4-(3,4-dimethyl-cyclohexyloxy)-benzonitrile;
xli) 2-chloro-4-(2,3-dimethyl-cyclohexyloxy)-benzonitrile;
xlii) 2-chloro-4-(2,6-dimethyl-cyclohexyloxy)-benzonitrile;
xliii) 3-chloro-4-(4-methyl-cyclohexyloxy)-benzonitrile;
xliv) 2-chloro-4-(2-phenyl-cyclohexyloxy)-benzonitrile;
xlv) 3-chloro-4-(4-methyl-cyclohexyloxy)-benzonitrile;
xlvi) 2-chloro-4-(2-isopropyl-5-methyl-cyclohexyloxy)-benzonitrile;
xlvii) 4-(bicyclo[2.2.1]hept-2-yloxy)-2-chloro-benzonitrile;
xlviii) 3-chloro-4-(2,3-dimethyl-cyclohexyloxy)-benzonitrile;
xlix) 2-chloro-4-(3,5-dimethyl-cyclohexyloxy)-benzonitrile;
l) 3-chloro-4-(2-methyl-cyclopentyloxy)-benzonitrile
li) 2-chloro-4-(2-methyl-cyclopentyloxy)-benzonitrile;
lii) 2-chloro-4-cyclobutyloxy-benzonitrile;
liii) 4-(2-ethoxy-cyclohexyloxy)-2-trifluoromethyl-benzonitrile;
liv) 4-(2-methoxy-cyclohexyloxy)-2-trifluoromethyl-benzonitrile;
lv) 2-chloro-4-(3-hydroxy-cyclohexyloxy)-benzonitrile, and;
lvi) 4-(2-allyloxy-cyclohexyloxy)-2-trifluoromethyl-benzonitrile;
lvii) 4-(2-cyano-cyclohexyloxy)-2-trifluoromethyl-benzonitrile;
lviii) (trans)-(+)-4-(2-cyano-cyclohexyloxy)-2-trifluoromethyl-benzonitrile; and,
lix) (trans)-(−)-4-(2-cyano-cyclohexyloxy)-2-trifluoromethyl-benzonitrile.

Synthesis

The compounds of Formula I can be prepared using methods known in the art for the preparation of ethers. The reader's attention is directed to European Patent Application Number 58932, published Sep. 1, 1982, the contents of which are hereby incorporated by reference for a description of such reactions. Scheme I below provides an overview of one such technique:

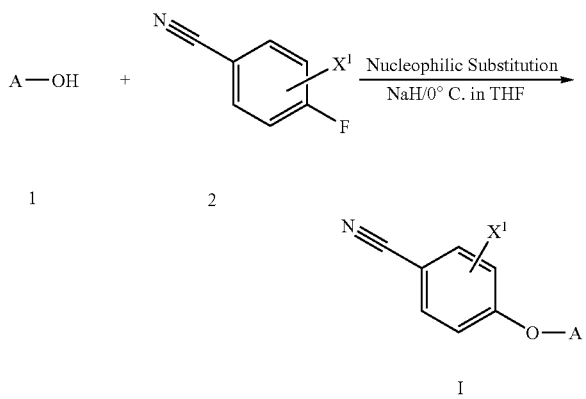

SCHEME I

As depicted above, one of the starting materials is an alcohol as depicted by structure 1. A should be represented by the same substituent as is desired in the final product. These alcohols are known in the art. Many may be purchased from known commercial sources. Alternatively, they can be prepared as described in the literature.

The other starting material is a 4-fluoro-benzonitrile as depicted by structure 2. $X^1$ should be represented by the same substituent as desired in the final product. These benzonitriles are known in the art and may be synthesized as described by Japanese Patent Application Number 01097937.

The nucleophilic substitution depicted above may be carried out as is known in the art. The alcohol of structure 1 is contacted with a slight excess of a base, such as sodium hydride potassium t-butoxide, etc., to produce an alkoxide ion. The reaction is carried out in an aprotic solvent, such as tetrahydrofuran, under an inert atmosphere (typically nitrogen) at a temperature of about 0° C. The alcohol is stirred with the base for a period of time ranging from 5 to 60 minutes.

One equivalent of the 4-fluoro-benzonitrile of structure 2 is then added to the reaction medium and the reactants are stirred for a sufficient period of time to allow the alkoxide ion to displace the fluorine from the benzonitrile. This typically takes from 30 minutes to 24 hours. The reaction is typically allowed to warm to room temperature.

The desired product of Formula I can be recovered by extraction, evaporation, or other techniques known in the art. It may then be optionally purified by chromatography, recrystallization, distillation, or other techniques known in the art.

As would be appreciated by those skilled in the art, some of the methods useful for the preparation of such compounds, as discussed above, may require protection of a particular functionality, e.g., to prevent interference by such functionality in reactions at other sites within the molecule or to preserve the integrity of such functionality. The need for, and type of, such protection is readily determined by one skilled in the art, and will vary depending on, for example, the nature of the functionality and the conditions of the selected preparation method. See, e.g., T. W. Greene, *Protective Groups in Organic Synthesis*, John Wiley & Sons, New York, 1991.

Some of the compounds of this invention are acidic and they form salts with pharmaceutically acceptable cations. Some of the compounds of this invention are basic and form salts with pharmaceutically acceptable anions. All such salts are within the scope of this invention and they can be prepared by conventional methods such as combining the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate.

The compounds are obtained in crystalline form according to procedures known in the art, such as by dissolution in an appropriate solvent(s) such as ethanol, hexanes or water/ethanol mixtures.

Medical and Cosmetic Uses

The compounds of Formula I are androgen receptor modulators. They can be used to alleviate conditions associated with inappropriate activation of the androgen receptor. Compounds acting as androgen antagonists may be used to treat, or alleviate, hormone dependent cancers such as prostate carcinomas, benign hyperplasia of the prostate, acne, hirsutism, excess sebum, alopecia, hypertrichosis, precocious puberty, prostamegaly, virilization, and polycystic ovary syndrome. Compounds acting as partial agonists, or full agonists, may be used to treat, or alleviate, male hypogonadism, male sexual dysfunction (impotence, male dysspemtatogenic sterility), abnormal sex differentiation (male hermaphroditism), male delayed puberty, male infertility, aplastic anemia, hemolytic anemia, sickle cell anemia, idiopathic thrombocytopenic purpura, myelofibrosis, renal anemia, wasting diseases (post operative, malignant tumor, trauma, chronic renal disease, burn or AIDS induced), abatement of pain in terminal carcinoma of female genitalia, inoperable breast cancer, mastopathy, endometriosis, female sexual dysfunction, osteoporosis, wound healing and muscle tissue repair.

In order to exhibit the therapeutic properties described above, the compounds need to be administered in a quantity sufficient to modulate activation of the androgen receptor. This amount can vary depending upon the particular disease/condition being treated, the severity of the patient's disease/condition, the patient, the particular compound being administered, the route of administration, and the presence of other underlying disease states within the patient, etc. When administered systemically, the compounds typically exhibit their effect at a dosage range of from about 0.1 mg/kg/day to about 100 mg/kg/day for any of the diseases or conditions listed above. Repetitive daily administration may be desirable and will vary according to the conditions outlined above.

The compounds of the present invention may be administered by a variety of routes. They may be administered orally. The compounds may also be administered parenterally (i.e., subcutaneously, intravenously, intramuscularly, intraperitoneally, or intrathecally), rectally, or topically.

In a typical embodiment, the compounds are administered topically. Topical administration is especially appropriate for hirsutism, alopecia, acne and excess sebum. The dose will vary, but as a general guideline, the compound will be present in a dermatologically acceptable carrier in an amount of from about 0.01 to 50 w/w %, and more typically from about 0.1 to 10 w/w %. The dermatological preparation will be applied to the affected area from 1 to 4 times daily. "Dermatologically acceptable" refers to a carrier which may be applied to the skin or hair, and which will allow the drug to diffuse to the site of action. More specifically, it refers the site where inhibition of activation of an androgen receptor is desired.

In a further embodiment, the compounds are used topically to relieve alopecia, especially androgenic alopecia. Androgens have a profound effect on both hair growth and hair loss. In most body sites, such as the beard and pubic skin, androgens stimulate hair growth by prolonging the growth phase of the hair cycle (anagen) and increasing follicle size. Hair growth on the scalp does not require androgens but, paradoxically, androgens are necessary for balding on the scalp in genetically predisposed individuals (androgenic alopecia) where there is a progressive decline in the duration of anagen and in hair follicle size. Androgenic alopecia is also common in women where it usually presents as a diffuse hair loss rather than showing the patterning seen in men.

While the compounds will most typically be used to alleviate androgenic alopecia, the invention is not limited to this specific condition. The compounds may be used to alleviate any type of alopecia. Examples of non-androgenic alopecia include alopecia areata, alopecia due to radiotherapy or chemotherapy, scarring alopecia, stress related alopecia, etc. As used in this application, "alopecia" refers to partial or complete hair loss on the scalp.

Thus, the compounds can be applied topically to the scalp and hair to prevent, or alleviate balding. Further, the compound can be applied topically in order to induce or promote the growth of hair on the scalp.

In a further embodiment of the invention, a compound of Formula I is applied topically in order to prevent the growth of hair in areas where such hair growth is not desired. One such use will be to alleviate hirsutism. Hirsutism is excessive hair growth in areas that typically do not have hair (i.e. a female face). Such inappropriate hair growth occurs most commonly in women and is frequently seen at menopause. The topical administration of the compounds will alleviate this condition leading to a reduction, or elimination of this inappropriate, or undesired, hair growth.

The compounds may also be used topically to decrease sebum production. Sebum is composed of triglycerides, wax esters, fatty acids, sterol esters and squalene. Sebum is produced in the acinar cells of the sebaceous glands and accumulates as these cells age. At maturation, the acinar cells lyse, releasing sebum into the lumenal duct so that it may be deposited on the surface of the skin.

In some individuals, an excessive quantity of sebum is secreted onto the skin. This can have a number of adverse consequences. It can exacerbate acne, since sebum is the primary food source for Propionbacterium acnes, the causative agent of acne. It can cause the skin to have a greasy appearance, typically considered cosmetically unappealing.

Formation of sebum is regulated by growth factors and a variety of hormones including androgen. The cellular and molecular mechanism by which androgens exert their influence on the sebaceous gland has not been fully elucidated. However, clinical experience documents the impact androgens have on sebum production. Sebum production is significantly increased during puberty, when androgen levels are their highest. Anti-androgens, such as finasteride, have been shown to decrease androgen secretion. For additional information on sebum production and androgens role in skin metabolism, see Moshell et al, Progress in Dermatology, vol. 37, No. 4, December 2003.

Thus, the compounds of formula I inhibit the secretion of sebum and thus reduce the amount of sebum on the surface of the skin. The compounds can be used to treat a variety of dermal diseases such as acne or seborrheic dermatitis.

In addition to treating diseases associated with excess sebum production, the compounds can also be used to achieve a cosmetic effect. Some consumers believe that they are afflicted with overactive sebaceous glands. They feel that their skin is oily and thus unattractive. These individuals can utilize the compounds of Formula I to decrease the amount of sebum on their skin. Decreasing the secretion of sebum will alleviate oily skin in individuals afflicted with such conditions.

In a further embodiment, those compounds acting as partial agonists, or full agonists, may be used to treat, or alleviate, osteoporosis. Osteoporosis is characterized by bone loss, resulting from an imbalance between bone resorption (destruction) and bone formation, which starts in the fourth decade and continues throughout life at the rate of about 1-4% per year (Eastell, Treatment of postmenopausal osteoporosis, New Eng. J. Med. 338: 736, 1998). In the United States, there are currently about 20 million people with detectable fractures of the vertebrae due to osteoporosis. In addition, there are about 250,000 hip fractures per year due to osteoporosis, associated with a 12%-20% mortality rate within the first two years, while 30% of patients require nursing home care after the fracture and many never become fully ambulatory again. In postmenopausal women, estrogen deficiency leads to increased bone resorption resulting in bone loss in the vertebrae of around 5% per year, immediately following menopause. Thus, first line treatment/prevention of this condition is inhibition of bone resorption by bisphosphonates, estrogens, selective estrogen receptor modulators (SERMs) and calcitonin. However, inhibitors of bone resorption are not sufficient to restore bone mass for patients who have already lost a significant amount of bone. The increase in spinal BMD attained by bisphosphonate treatment can reach 11% after 7 years of treatment with alendronate. In addition, as the rate of bone turnover differs from site to site; higher in the trabecular bone of the vertebrae than in the cortex of the long bones, the bone resorption inhibitors are less effective in increasing hip BMD and preventing hip fracture. Therefore, osteoanabolic agents, which increase cortical/periosteal bone formation and bone mass of long bones, would address an unmet need in the treatment of osteoporosis especially for patients with high risk of hip fractures.

A number of studies demonstrate that androgens are osteoanabolic in women and men. Anabolic steroids, such as nandrolone decanoate or stanozolol, have been shown to increase bone mass in postmenopausal women. Beneficial effects of androgens on bone in post-menopausal osteoporosis are well documented in recent studies using combined testosterone and estrogen administration (Hofbauer, et al., Androgen effects on bone metabolism: recent progress and controversies, Eur. J. Endocrinol. 140, 271-286, 1999). Thus those compounds of Formula I exhibiting agonist or partial agonist activity may be used to treat, or alleviate, osteoporosis, including primary osteoporosis such as senile, postmenopausal and juvenile osteoporosis, as well as secondary osteoporosis, such as osteoporosis due to hyperthyroidism or Cushing syndrome (due to corticosteroid treatment), acromegaly, hypogonadism, dysosteogenesis and hypophosphatasemia. Other bone related indications amendable to treat from androgen agonists include osteoporotic fracture, childhood idiopathic bone loss, alveolar bone loss, mandibular bone loss, bone fracture, osteotomy, periodontitis, or prosthetic ingrowth.

Those compounds acting as agonists, or partial agonists, can also be used to stimulate muscle mass in patients afflicted with wasting diseases, such as AIDS, cancer cachexia, burns, renal disease, etc. Patients suffering from trauma, bedsores, age, etc. can also benefits from the anabolic effects of androgens.

Co-Administration

In a further embodiment of the invention, the compounds of Formula I can be co-administered with other compounds to further enhance their activity, or to minimize potential side effects. For example, potassium channel openers, such as minoxidil, are known to stimulate hair growth and to induce anagen. Examples of other potassium channel openers include (3S,4R)-3,4-dihydro-4-(2,3-dihydro-2-methyl-3-oxopyridazin-6-yl)oxy-3-hydroxy-6-(3-hydroxyphenyl)sulphonyl-2,2,3-trimethyl-2H-benzo[b]pyran, diaxozide, and P1075 which is under development by Leo Pharmaceuticals. Such compounds can be co-administered with the compounds of Formula I to alleviate alopecia Thyroid hormone is also known to stimulate hair growth. Synthetic thyroid hormone replacements (i.e., thyromimetics) have also been shown to stimulate hair growth. Such thyromimetics have been described in the literature previously. The reader's attention is directed to European Patent Application No. 1262177, the contents of which are hereby incorporated by reference, for a discussion of such compounds and their use to alleviate alopecia. One particular compound of interest is 2-{4-[3-(4-Fluoro-benzyl)-4-hydroxy-phenoxy]-3,5-dimethyl-phenyl}-2H-[1,2,4]triazine-3,5-dione. Such compounds can be co-administered with the compounds of Formula I to alleviate alopecia.

Anti-androgens can work by a number of different mechanisms. For example, some compounds block the conversion of testosterone to 5-α-dihydrotestosterone, which is responsible for the biological effect in many tissues. 5-Alpha-reductase inhibitors, such as finasteride, have been shown to stimulate hair growth and to decrease sebum production. Finasteride is commercially available from Merck under the trade name Propecia®. Examples of other 5-α-reductase inhibitors include dutasteride (Glaxo Smithkline). Such compounds can be co-administered with the compounds of Formula I to alleviate alopecia and/or to decrease sebum production.

Protein kinase C inhibitors have also been shown to stimulate hair growth and induce anagen. Calphostin C, which is a selective inhibitor of protein kinase C, has been shown to induce anagen. Other selective protein kinase C inhibitors, such as hexadecylphosphocholine, palmitoyl-DL-carnitine chloride, and polymyxin B sulfate have also been shown to induce anagen. [Skin Pharmacol Appl Skin Physiol 2000 May-August; 13(3-4):133-42]. Any such protein kinase C inhibitor can be co-administered with a compound of Formula I to alleviate alopecia.

Immunophilins are a family of cytoplasmic proteins. Their ligands include cyclosporin and FK506. They are derived from fungi and were developed primarily for their potent immunosuppressive properties. Cyclosporin binds to the proteins, cyclophilins, while FK506 binds to FK binding proteins (FKBPs). All of these compounds have been shown to stimulate hair growth and induce anagen. Any such immunophilin ligands can be co-administered with a compound of Formula I to alleviate alopecia.

Acyl CoA cholesterol acyl transferase (ACAT) inhibitors were initially evaluated for the treatment of elevated serum cholesterol. It was subsequently discovered that these compounds decrease sebum production (U.S. Pat. No. 6,133,326). Any such ACAT inhibitor can be co-administered with a compound of formula I to decrease sebum production, alleviate oily skin, etc.

Antibiotics, such as tetracycline and clindamycin, have been used to alleviate acne. The antibiotic eradicates the microorganism, Propionbacterium acnes, leading to a reduction in the patient's acne. The compounds of Formula I can be co-administered with any antibiotic suitable for the treatment of acne.

Retinoids, such as isotretinoin, have been shown to decrease sebum production and are used to treat acne. These retinoids can be co-administered with a compound of Formula I in order to decrease sebum production and/or to treat acne.

Estrogen and progesterone have each been shown to decrease sebum production. These compounds, or any synthetic agonist of such compounds, may be co-administered with a compound of formula I in order to decrease sebum production.

As used in this application, co-administered refers to administering a compound of Formula I with a second medicinal, typically having a differing mechanism of action, using a dosing regimen that promotes the desired result. This can refer to simultaneous dosing, dosing at different times during a single day, or even dosing on different days. The compounds can be administered separately or can be combined into a single formulation. Techniques for preparing such formulations are described below.

Formulations

If desired, the compounds can be administered directly without any carrier. However, to ease administration, they will typically be formulated into pharmaceutical carriers. Likewise, they will most typically be formulated into dermatological, or cosmetic carriers. In this application the terms "dermatological carrier" and "cosmetic" carrier are being used interchangeably. They refer to formulations designed for administration directly to the skin or hair.

Pharmaceutical and cosmetic compositions can be manufactured utilizing techniques known in the art. Typically an effective amount of the compound will be admixed with a pharmaceutically/cosmetically acceptable carrier.

For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations.

In another embodiment, the compounds of Formula I can be tableted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the active ingredient in an aqueous or non-aqueous pharmaceutically acceptable solvent, which may also contain suspending agents, sweetening agents, flavoring agents, and preservative agents as are known in the art.

For parenteral administration, the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, buffers, etc., as are known in the art. When the compounds are being administered intrathecally, they may also be dissolved in cerebrospinal fluid as is known in the art.

The compounds of this invention will typically be administered topically. As used herein, topical refers to application of the compounds (and optional carrier) directly to the skin and/or hair. The topical composition according to the present invention can be in the form of solutions, lotions, salves, creams, ointments, liposomes, sprays, gels, foams, roller sticks, or any other formulation routinely used in dermatology.

Thus, a further embodiment relates to cosmetic or pharmaceutical compositions, in particular dermatological compositions, which comprise at least one of the compounds corresponding to Formula I above. Such dermatological compositions will contain from 0.001% to 10% w/w % of the compounds in admixture with a dermatologically acceptable carrier, and more typically, from 0.1 to 5 w/w % of the compounds. Such compositions will typically be applied from 1 to 4 times daily. The reader's attention is directed to *Remington's Pharmaceutical Science*, Edition 17, Mack Publishing Co., Easton, Pa. for a discussion of how to prepare such formulations.

The compositions according to the invention can also consist of solid preparations constituting cleansing soaps or bars. These compositions are prepared according to the usual methods.

The compounds can also be used for the hair in the form of aqueous, alcoholic or aqueous-alcoholic solutions, or in the form of creams, gels, emulsions or mousses, or alternatively in the form of aerosol compositions also comprising a propellant under pressure. The composition according to the invention can also be a hair care composition, and in particular a shampoo, a hair-setting lotion, a treating lotion, a styling cream or gel, a dye composition, a lotion or gel for preventing hair loss, etc. The amounts of the various constituents in the dermatological compositions according to the invention are those conventionally used in the fields considered.

The medicinal and cosmetics containing the compounds of the invention will typically be packaged for retail distribution (i.e. an article of manufacture). Such articles will be labeled and packaged in a manner to instruct the patient how to use the product. Such instructions will include the condition to be treated, duration of treatment, dosing schedule, etc.

The compounds of Formula I may also be admixed with any inert carrier and utilized in laboratory assays in order to determine the concentration of the compounds within the serum, urine, etc., of the patient as is known in the art. The compounds may also be used as a research tool.

Use in Livestock

In addition to the therapeutic and cosmetic uses described above, the compounds may also be used to promote the growth of animals, especially livestock. The compounds will increase the rate at which the animals gain weight, increase the leanness of the resulting meat and improve the efficiency of feed utilization. This may be accomplished by administering an effective amount of a compound of Formula I to an animal receiving adequate nutrition to support growth (i.e. sufficient calories, amino acids, vitamins, minerals, essential fats, etc).

To simplify administration, the compound is typically mixed with animal feeds or prepared in the form of an animal-feed premix, concentrate, or supplement which can be blended with animal feeds. Regardless of the procedure selected, the compound will typically be present at levels of from about 0.05 to 500 ppm in the feed.

Animal-feed premixes, supplements or concentrates can be prepared by mixing on a weight basis about 0.5 to 50% of a compound with about 50 to 99.5% of an edible diluent. Diluents suitable for use in the manufacture of animal-feed supplements, concentrates, and premixes include the following: corn meal, soybean meal, bone meal, alfalfa meal, cottonseed oil meal, urea, molasses, and other similar materials. Use of the diluents in feed supplements, concentrates, and premixes improves uniformity of distribution of the active ingredient in the finished feed.

Feeds for swine, cattle, sheep, fish, and goats typically contains about 0.05 to 400 grams of active ingredient per ton of feed. Poultry and domestic-pet feeds range from about 0.05 to 400 grams per ton of feed.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention. The following examples and biological data is being presented in order to further illustrate the invention. This disclosure should not be construed as limiting the invention in any manner.

EXAMPLES

Example 1

4-(5-Hydroxy-5-methyl-bicyclo[2.2.1]hept-2-yloxy)-2-trifluoromethyl-benzonitrile

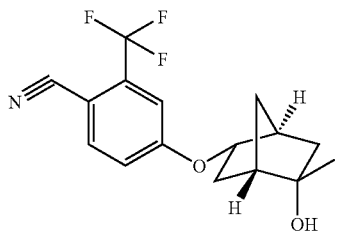

NaH (0.10 g, 1.75 mmol, 60% in mineral oil) was suspended in 15 ml of dry THF (tetrahydrofuran) at 0° C. under nitrogen ($N_2$) gas, then 4-fluoro-2-(trifluoromethyl)-benzonitrile (0.3 g, 1.59 mmol) was added, this mixture was stirred at 0° C. under $N_2$ for 10 minutes, before adding 2-methyl-bicyclo[2.2.1]heptane-2,5-diol (0.23 g, 1.59 mmol). The reaction mixture was stirred at 0° C. for 2 hours (h), then room temperature (RT) for 1 h. It was quenched with 50 ml of distilled water, extracted with ethyl acetate (3×30 ml), the organic layer was washed with saturated $NaHCO_3$ (three times), the solvent was removed to yield the crude product, it was purified by column with hexane:ethyl acetate=1:1 as the elute.

(MS: 312.1 (M+1 for $C_{16}H_{16}NF_3O_2$) LCMS: C-18 Column (25% $H_2O$/75% $CH_3CN$), Ret. Time: 1.31 min Purity: 100%)

Example 2

4-(trans-2-Methyl-cyclopentyloxy)-2-trifluoromethyl-benzonitrile

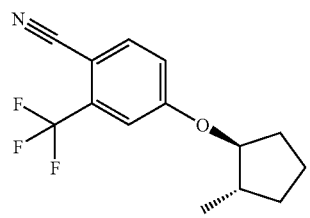

Trans-2-Methylcylopentanol (50 mg, 0.5 mmol) was added to a flame dried round bottom flask under nitrogen containing 0.5 mL of dry tetrahydrofuran ("THF") and cooled to 0° C. A 1.0 M solution of potassium t-butoxide in t-butanol (0.5 mL) was added dropwise and the reaction mixture stirred at 0° C. for 0.5 h. The above solution was then transferred via syringe to a flask containing 2-Trifluoromethyl-4-fluoro-benzonitrile (95 mg, 0.5 mmol) in 0.5 mL of THF at 0° C. The mixture was stirred at 0° C. for 3 h, warmed to room temperature and stirred for 16 h. The reaction mixture was then cooled to 0° C., poured into a seperatory funnel containing 8 mL of water, and extracted with 10 mL of methyl tert-butyl ether. The organic phase was washed with water, brine, dried (MgSO4), concentrated in vacuo, and the residue purified by reverse phase HPLC (Shimadzu) to give 112 mg 4-(trans-2-Methyl-cyclopentyloxy)-2-trifluoromethyl-benzonitrile. GC/MS: 269 (M/Z for $C_{14}H_{14}F_3NO$).

Example 3

4-(2-(R)-Phenyl-1-(S)-cyclohexyloxy)-2-trifluoromethyl-benzonitrile

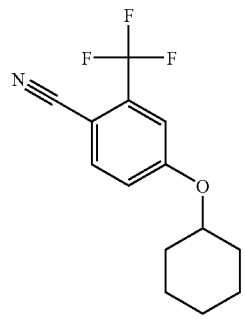

The title compound was prepared according to the procedure described in Example 2, except that 1-(S)-2-(R)-Phenyl-cyclohexyanol was used as the starting alcohol to give 66 mg of the desired product. GC/MS: 345 (M/Z for $C_{20}H_{18}F_3NO$).

Examples 4-18, 20-23 and 40-68

The products of Examples 4-18, 20-22 and 40-68 and were prepared by combinatorial chemistry, using the general synthetic method of Reaction Scheme I. One of the reactants was 4-fluoro-2-(trifluoromethyl)-benzonitrile. The other reactant was an appropriate alcohol as described by structure 1, above, in which A corresponds to the cycloalkyl moiety present in the final product. A variety of combinatorial methods were used. The specifics of each are described below. The letter identifying each method is used in the examples below to explain how the compounds were made, purified, characterized, etc.

Combinatorial Methods

I) Synthetic Methods

Method A

To a Bohdan mini-block reaction tube containing a solution of 4-fluoro-2-(trifluoromethyl)benzonitrile (0.3 mmol) and the appropriate cycloalkane of structure 1 (0.3 mmol) in anhydrous THF (tetrahydrofuran) (1.3 mL) was added a 0.6M (molar) slurry of sodium hydride in anhydrous THF (2 eqs, 0.6 mmol). The Bohdan mini-block was capped and the reaction was shaken at ambient temperature for 16H. 500 uL of methanol and 245 mgs of macroporous tosic acid resin "MP-TsOH" (1.53 mmol/g, 1.25 eq, 0.375 mmol) was added and the reaction was shaken at ambient temperature 3H. Reaction was filtered, washing solids well with tetrahydrofuran, and concentrated utilizing a Genevac HT-12. Sample was purified via reverse phase HPLC.

Method B

To a Bohdan mini-block reaction tube containing a solution of 4-fluoro-2-(trifluoromethyl)benzonitrile (0.3 mmol) and the appropriate cycloalkane of structure 1 (0.3 mmol) in anhydrous THF (1.3 mL) was added a 0.6M slurry of sodium hydride in anhydrous THF (2 eqs, 0.6 mmol). The Bohdan mini-block was capped and the reaction was shaken at ambient temperature for 16H. 500 uL of methanol and 100 mgs of MP-TsOH (4.07 mmol/g, 1.35 eq, 0.41 mmol) was added and the reaction was shaken at ambient temperature 20H. Reaction was filtered, washing solids well with methanol, and concentrated utilizing a Genevac HT-12. Sample was purified via reverse phase HPLC.

Method C

To a Bohdan mini-block reaction tube containing a solution of 4-fluoro-2-(trifluoromethyl)benzonitrile (0.3 mmol) and the appropriate cycloalkane of structure 11 (0.3 mmol) in anhydrous THF (1.3 mL) was added a 0.6M slurry of sodium hydride in anhydrous THF (2 eqs, 0.6 mmol). The Bohdan mini-block was capped and the reaction was shaken at ambient temperature for 16H. 500 uL of methanol and 100 mgs of MP-TsOH (4.07 mmol/g, 1.35 eq, 0.41 mmol) was added and the reaction was shaken at ambient temperature 60H. Reaction was filtered, washing solids well with methanol, and concentrated utilizing a Genevac HT-12. Sample was purified via reverse phase HPLC.

Method D

To 1 mL of a 0° C. 0.3M solution of 4-fluoro-2-(trifluoromethyl)benzonitrile in tetrahydrofuran "THF" (0.3 mmol) was added 0.6 mL of a 1 M solution of potassium t-butoxide in THF (0.6 mmol) and 0.3 mL of a 1.0M solution of the corresponding cycloalkane of structure 1 (0.3 mmol) in THF. The resultant mixtures were shaken and allowed to warm to room temperature over approximately 72 hours. The solvent was removed in vacuo using a Genevac HT-12 to obtain a sample that was then purified by reverse phase HPLC Method E To 1 mL of a 0.3M solution of 4-fluoro-2-(trifluoromethyl) benzonitrile in tetrahydrofuran "THF" (0.3 mmol) was added a 1 mL slurry of a 0.63 M solution of sodium hydride (60%) in THF (0.63 mmol) and 0.3 mL of a 1.0M solution of the appropriate cycloalkane of structure 1 (0.3 mmol) in THF. The resultant mixtures were shaken at room temperature over approximately 18 hours. The reactions were quenched with methanol and macroporous tosic acid resin (0.3 mmol, loading 1.53 mmol/g). The resultant mixture was shaken at room termperature for approximately 18 hours. Filtered the reaction, rinsing with THF. Removed in vacuo using a Genevac HT-12 to obtain a sample that was then purified by reverse phase HP.

II) HPLC Methods (High Performance Liquid Chrmoatography)

Method A

Column: BHK 30×100 mm ODS-OB 5 um $C_{18}$

Flow Rate: 30 mL/min

Solvent: A=Acetonitrile w/3% 1-Propanol; B=Water w/3% 1-Propanol

Method: 0-6.0 min: 10% A, 90% B; 6.0-10.5 min: 100% A

Method B

Column: YMC 30×100 mm ODS-A 5 um $C_{18}$

Flow Rate: 30 mL/min

Solvent: A=Acetonitrile w/3% 1-Propanol; B=Water w/3% 1-Propanol

Method: 0-6.5 min: 10% A, 90% B; 6.5-10.5 min: 100% A

Method C

Column: Xterra 30×100 mm 5 um $C_{18}$

Flow Rate: 30 mL/min

Solvent: A=Acetonitrile w/3% 1-Propanol; B=Water w/3% 1-Propanol

Method: 0-6.5 min: 15% A, 85% B; 6.5-10.5 min: 100% A

Method D

Column: YMC 30×100 mm ODS-A 5 um $C_{18}$

Flow rate: 30 mL/min

Solvent: A=Acetonitrile w/3% 1-Propanol; B=Water w/3% 1-Propanol

Method: 0-7 min: 10% A, 90% B; 7-10 min: 100% A

Method E

Column: YMC 30×100 mm ODS-A 5 um $C_{18}$

Flow rate: 30 mL/min

Solvent: A=Acetonitrile w/3% 1-Propanol; B=Water w/3% 1-Propanol

Method: 0-6 min: 10% A, 90% B; 6-10.5 min: 100% A

III) LCMS (Liquid Chromoatography Mass Spectrum) Methods

Method A

LCMS: Aqua C18 50 mm×4.6 mm, 3 mm column (Solvent: A=Water w/10 mM Ammonium Acetate; B=Acetonitrile w/0.005M Formic Acid, Method: 0-2 min: 85% A, 15% B; 2-5.1 min: 2% A, 98% B; 5.1-7 min: 85% A, 15% B Method B LCMS: Atlantis C18 50 mm×4.6 mm, 3 mm column (Solvent: A=Water w/0.005M Formic Acid; B=Acetonitrile w/0.005M Formic Acid, Method: 0-3 min: 95% A, 5% B; 3-5.1 min: 2% A, 98% B; 5.1-7 min: 95% A, 5% B Method C LCMS: Polaris C8 50 mm×4.6 mm, 3 mm column (Solvent: A=Water w/10 mM Ammonium Acetate; B=Acetonitrile w/0.005M Formic Acid, Method: 0-2 min: 95% A, 5% B; 2-5.1 min: 2% A, 98% B; 5.1-7 min: 95% A, 5% B Method D LCMS: YMC-Phenyl 50 mm×4.6 mm, 3 mm column (Solvent: A=Water w/0.005M Formic Acid; B=Acetonitrile w/0.005M Formic Acid, Method: 0-3.5 min: 90% A, 10% B; 3.5-5.1 min: 2% A, 98% B; 5.1-7 min: 90% A, 10% B Method E LCMS: YMC Pack Pro C18, 50 mm×4.6 mm, 3 mm column (Solvent: A=Water w/0.1M Formic Acid; B=Acetonitrile w/0.1M Formic Acid, Method: 0-1.5 min: 95% A, 5% B; 1.5-4.1 min: 2% A, 98% B; 4.1-7 min: 95% A, 5% B.

Method F

LCMS: YMC ODS-AQ, 50 mm×4.6 mm, 3 mm column (Solvent: A=Water w/0.1M Formic Acid; B=Acetonitrile w/0.1M Formic Acid, Method: 0-2.5 min: 80% A, 20% B; 2.5-5.1 min: 2% A, 98% B; 5.1-7 min: 80% A, 20% B Example 4

4-(1-Allyl-cyclohexyloxy)-2-trifluoromethyl-benzonitrile

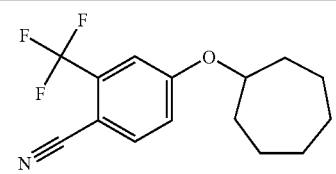

| Synthesis- | Method D |
| HPLC- | Method D |
| LCMS- | Method E |

MS: 310.23 (M+1 for $C_{17}H_{18}F_3NO$); RT. 3.13 Purity: 100.

Example 5

4-cycloheptyloxy-2-trifluoromethyl-benzonitrile

| Synthesis- | Method A |
| HPLC- | Method A |
| LCMS- | Method A |

MS: 284.27 (M+1 for $C_{15}H_{16}F_3NO$); RT. 3.41 Purity: 100.

Example 6

4-(2,3-Dimethyl-cyclohexyloxy)-2-trifluoromethyl-benzonitrile

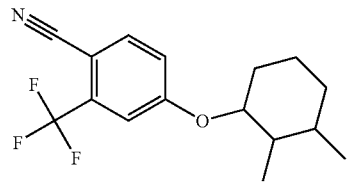

| Synthesis- | Method D |
| HPLC- | Method D |
| LCMS- | Method E |

MS: 298.22 M+1 for $C_{16}H_{18}F_3NO$); RT. 3.2 Purity: 100.

Example 7

4-(2-Ethyl-cyclohexyloxy)-2-trifluoromethyl-benzonitrile

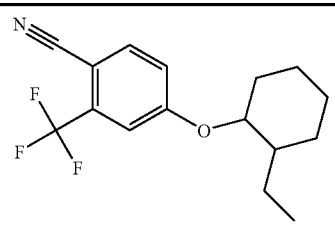

| Synthesis- | Method E |
| HPLC- | Method E |
| LCMS- | Method F |

MS: 298.22 (M+1 for $C_{16}H_{18}F_3NO$); RT. 3.99 Purity: 100

Example 8

4-(2-Methyl-cyclohexyloxy)-2-trifluoromethyl-benzonitrile

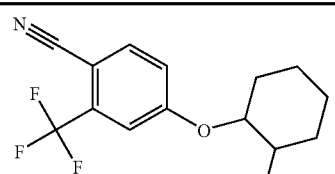

| Synthesis- | Method A |
| HPLC- | Method A |
| LCMS- | Method A |

MS: 284.29 (M+1 for $C_{15}H_{16}F_3NO$); RT. 3.39 Purity: 100.

Example 9

(1S,2R)-4-(2-Methyl-cyclohexyloxy)-2-trifluoromethyl-benzonitrile

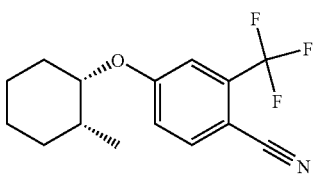

| Synthesis- | Method A |
| HPLC- | Method A |
| LCMS- | Method A |

MS: 284.29 (M+1 for $C_{15}H_{16}F_3NO$); RT. 3.42 Purity: 100.

Example 10

4-Cyclopentyl-2-trifluoromethyl-benzonitrile

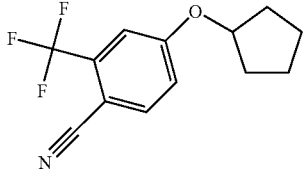

| Synthesis- | Method B |
| HPLC- | Method B |
| LCMS- | Method B |

MS: 256.25 (M+1 for $C_{13}H_{12}F_3NO$); RT. 4.07 Purity: 100.

Example 11

4-Cyclohexyloxy-2-trifluoromethyl-benzonitrile

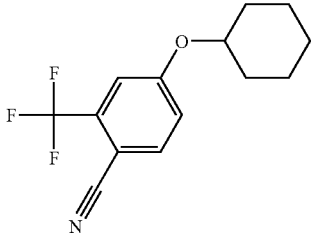

| Synthesis- | Method B |
| HPLC- | Method B |
| LCMS- | Method B |

MS: 270.29 (M+1 for $C_{14}H_{14}F_3NO$); RT. 4.19 Purity: 100.

Example 12

4-(2,6-Dimethyl-cyclohexyloxy)-2-trifluoromethyl-benzonitrile

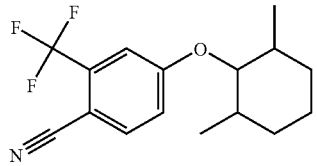

| Synthesis- | Method B |
| HPLC- | Method B |
| LCMS- | Method B |

MS: 298.3 (M+1 for $C_{16}H_{18}F_3NO$); RT. 4.44 Purity: 100.

Example 13

(1S,2S,5S)-4-(5-Isopropenyl-2-methyl-cyclohexyloxy)-2-trifluoromethyl-benzonitrile

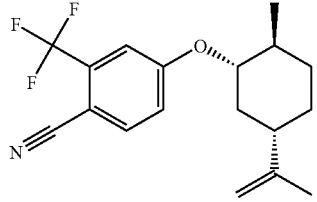

| Synthesis- | Method B |
| HPLC- | Method B |
| LCMS- | Method B |

MS: 324.32 (M+1 for $C_{18}H_{20}F_3NO$); RT. 4.56 Purity: 100.

Example 14

-4-(2-Cyano-cyclohexyloxy)-2-trifluoromethyl-benzonitrile

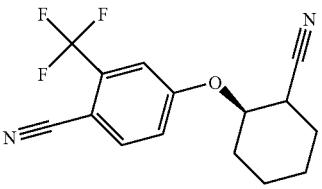

| Synthesis- | Method B |
| HPLC- | Method B |
| LCMS- | Method B |

MS: 295.26 (M+1 for $C_{15}H_{13}F_3N_2O$); RT. 3.67 Purity: 100.

Example 15

4-(4-Methoxy-cyclohexyloxy)-2-trifluoromethyl-benzonitrile

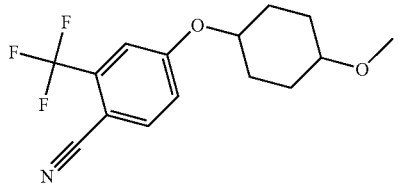

| Synthesis- | Method B |
| --- | --- |
| HPLC- | Method B |
| LCMS- | Method B |

MS: 300.28 (M+1 for $C_{15}H_{16}F_3NO_2$); RT. 3.84 Purity: 100.

Example 16

(1S,4S)-4-(2-Methyl-cyclopentyloxy)-2-trifluoromethyl-benzonitrile

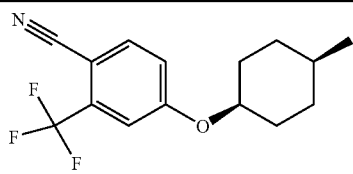

| Synthesis- | Method B |
| --- | --- |
| HPLC- | Method A |
| LCMS- | Method C |

MS: 284.27 (M+1 for $C_{15}H_{16}F_3NO$); RT. 2.44 Purity: 100.

Example 17

(1S,2S)-4-(2-Methyl-cyclopentyloxy)-2-trifluoromethyl-benzonitrile

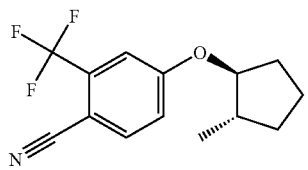

| Synthesis- | Method C |
| --- | --- |
| HPLC- | Method C |
| LCMS- | Method D |

MS: 270.2 (M+1 for $C_{14}H_{14}F_3N_0$); RT. 3.47 Purity: 100.

Example 18

4-Cyclobutoxy-2-trifluoromethyl-benzonitrile

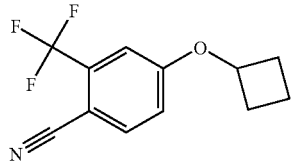

| Synthesis- | Method C |
| --- | --- |
| HPLC- | Method C |
| LCMS- | Method C |

MS: 242.2 (M+1 for $C_{12}H_{10}F_3N_0$); RT. 3.27 Purity: 100

Example 19

1S,5S)-2-Chloro-4-(5-hydroxy-5-methyl-bicyclo[2.2.1]hept-2-yloxy)-benzonitrile

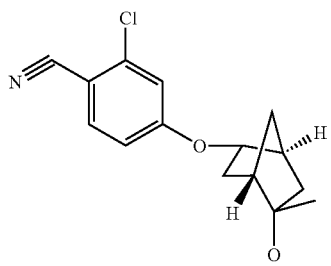

NaH was suspended in 15 ml of dry THF at 0° C. under $N_2$ gas, then 4-fluoro-2-(trifluoromethyl)-benzonitrile (1.0 g, 5.18 mmol) was added, this mixture was stirred at 0° C. under $N_2$ for 10 min before adding (2R, 3R)-2,3-butanediol (0.23 g, 2.46 mmol). The reaction mixture was stirred at 0° C. for 2 h, then RT for 1 h. It was quenched with 50 ml of distilled water, extracted with ethyl acetate (3×30 ml), the organic layer was washed with saturated $NaHCO_3$ (three times), the solvent was removed to yield the crude product, it was purified by column with hexane:ethyl acetate=5:1 as the elute.

MS: 429.0 (M+1 for $C_{20}H_{14}N_2F_6O_2$) LCMS: C-18 Column (25% $H_2O$ /75% $CH_3CN$), Ret. Time: 1.36 min Purity: 100%.

Example 20

2-Chloro-4-(2,3-dimethyl-cyclohexyloxy)-benzonitrile

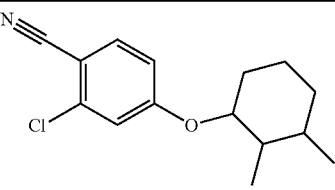

| Synthesis- | Method D |
| --- | --- |
| HPLC- | Method D |
| LCMS- | Method E |

MS: 264.19 (M+1 for $C_{15}H_{18}ClNO$); RT 3.27 min. Purity: 100

Example 21

4-(1-Butyl-cyclopentyloxy)-2-chloro-benzonitrile

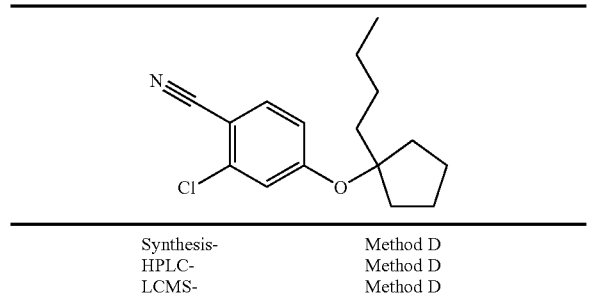

| Synthesis- | Method D |
| --- | --- |
| HPLC- | Method D |
| LCMS- | Method D |

MS: 278.22 (M+1 for $C_{16}H_{20}ClNO$); RT 3.42 min. Purity: 100

Example 22

2-Chloro-4-(2-ethyl-cyclohexyloxy)-benzonitrile

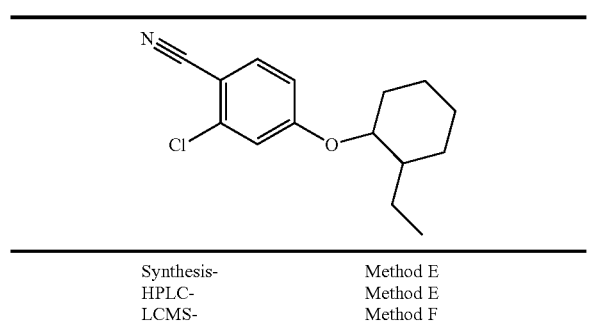

| Synthesis- | Method E |
| --- | --- |
| HPLC- | Method E |
| LCMS- | Method F |

MS: 264.19 (M+1 for $C_{15}H_{18}ClNO$); RT 4.04 min. Purity: 100.

Example 23

2-Chloro-4-(3-methyl-cyclopentyloxy)-benzonitrile

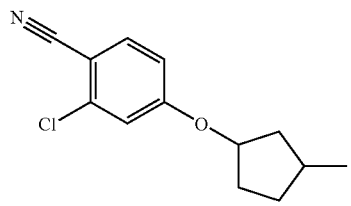

A 1.0 M solution of potassium t-butoxide in t-butanol (0.3 mL) was added to a 8 mL vial fitted with a septa cap containing 0.3 mL of dry THF and 30 mg (0.3 mmoles) of 3-hydroxy cylcopentanol at 5° C. The mixture was stirred for 0.5 h at 5° C., after which time 0.3 mL of a 1.0 M THF solution of 4-fluoro-2-chloro-benzonitrile was added. The reaction was stirred at 5° C. for 3 h and then allowed to warm to room temperature and stirred overnight at room temperature. The reaction mixture was cooled to 0° C., and quenched with 2 mL of water, diluted with 2 mL of methyl tert-butyl ether. The vial was shaken vigourously and the phases allowed to separate. The aqueous layer was removed with a pipette, and the organic layer washed with another 2 mL of water. The organic phase was dried (MgSO4), concentrated in vacuo, and the residue purified by reverse phase HPLC (Shimadzu) to give 36 mg (52%) of the title compound. GC/MS: 235 (M/Z for $C_{13}H_{14}ClNO$).

Example 24

4-(R)-(Bicyclo[2.2.1]hept-2-yloxy)-2-chloro-benzonitrile

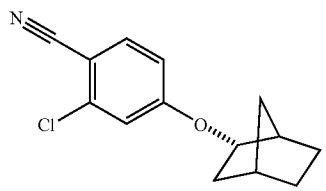

Example 24 was prepared by the similar method used in Example 23 except that (R)-2-Hydroxy-(Bicyclo[2.2.1]heptane) was utilized as the alcohol. GC/MS: 247 (M/Z for $C_{14}H_{14}ClNO$).

Example 25

4-(S)-(Bicyclo[2.2.1]hept-2-yloxy)-2-chloro-benzonitrile

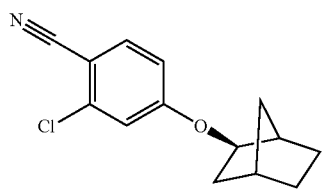

Example 25 was prepared by the similar method used in Example 23 except that (S)-2-Hydroxy-(Bicyclo[2.2.1]heptane) was utilized as the alcohol. GC/MS: 247 (M/Z for $C_{14}H_{14}ClNO$).

Example 26

2-Chloro-4-(3-hydroxy-cyclohexyloxy)-benzonitrile

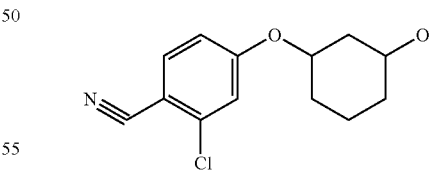

1,3-Cyclohexanediol (116 mg, 1.0 mmole) was added to a flame dried round bottom flask under nitrogen. The flask was then charged with 5 mL of dry acetonitrile, 26 mg of potassium fluoride on alumina (0.1 mmol), and 4-fluoro-2-chloro-benzonitrile (155 mg, 1.0 mmole) and heated at reflux for 16 h. Diethyl ether (15 ml) was added to the reaction mixture, which was then extracted with water (2×), dried (MgSO4) and concentrated. Purification using a chromatotron, eluting with 10% EtOAc/hex (ethylacetate and hexane) provided 22 mg of the title compound. GC/MS: 251 (M/Z for $C_{13}H_{14}ClNO_2$).

Example 27

2-Chloro-4-(2-ethyl-cyclohexyloxy)-benzonitrile

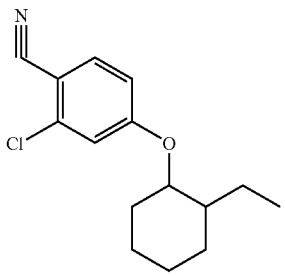

4-Fluoro-2-chloro-benzonitrile (122 mg, 0.79 mmole) was added to a flame dried round bottom flask under nitrogen containing 2 mL of dry dimethylformamide ("DMF") and 63 mg of 60% sodium hydride as an oil dispersion (1.6 mmol). 2-Ethylcyclohexanol. (100 mg, 0.79 mmole) dissolved in 1 mL of dry DMF was then added to the reaction vessel via syringe in a dropwise manner. The reaction was stirred at room temperature for 16 h, after which time 5 mL of water was added dropwise. The mixture was extracted twice with diethyl ether, washed with water, dried (MgSO4) and concentrated. Purification using a chromatotron eluting with 5% EtOAc/hex followed by 5% EtOAc/hex gave 155 mg of the title compound. GC/MS: 263 (M/Z for $C_{15}H_{18}ClNO$).

Example 28

2-Chloro-4-(2-methyl-cyclohexyloxy)-benzonitrile

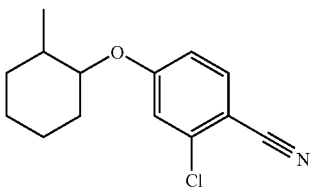

Example 28 was prepared by the similar method used in Example 23 except that 2-methylcyclohexanol was utilized as the alcohol to give 5.5 mg of the title compound. GC/MS: 249 (M/Z for $C_{14}H_{14}ClNO$).

Example 29

2-Chloro-4-(2-phenyl-cyclohexyloxy)-benzonitrile

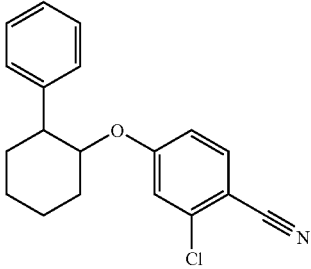

Example 29 was prepared by the similar method used in Example 23 except that 2-phenylcyclohexanol was utilized as the alcohol to give 4.9 mg of the title compound. GC/MS: 311 (M/Z for $C_{19}H_{18}ClNO$).

Example 30

2-Chloro-4-(2-(S)-methyl-(S)-cyclohexyloxy)-benzonitrile

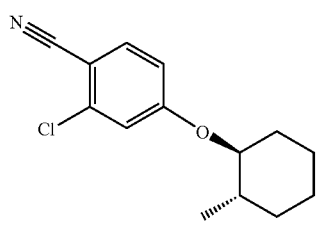

Example 30 was prepared by the similar method used in Example 23 except that 1-(S)-2-(S)-methyl-cyclohexanol was utilized as the alcohol to give 23 mg of the title compound. GC/MS: 249 (M/Z for $C_{19}H_{18}ClNO$).

Example 31

2-Chloro-4-(4-cis-methyl-cyclohexyloxy)-benzonitrile

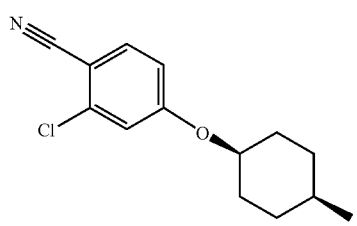

Example 31 was prepared by the similar method used in Example 23 except that 4-cis-methylcyclohexanol was utilized as the alcohol to give 60 mg of the title compound. GC/MS: 249 (M/Z for $C_{14}H_{16}ClNO$)

Example 32

2-Chloro-4-(4-cis-methyl-cyclohexyloxy)-benzonitrile

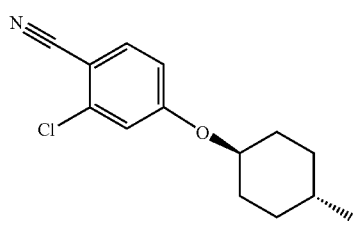

Example 32 was prepared by the similar method used in Example 23 except that 4-trans-methylcyclohexanol was utilized as the alcohol to give 41 mg of the title compound. GC/MS: 249 (M/Z for $C_{14}H_{16}ClNO$).

Example 33

2-Chloro-4-(2-(S)-phenyl-(S)-cyclohexyloxy)-benzonitrile

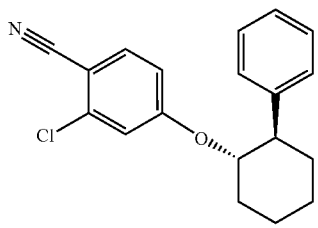

Example 33 was prepared by the similar method used in Example 23 except that 1-(S)-2-(S)-phenyl-cyclohexanol was utilized as the alcohol to give 49 mg of the title compound. GC/MS: 311 (M/Z for $C_{19}H_{18}ClNO$).

Example 34

2-Chloro-4-(cis-2-methoxy-cyclopentyloxy)-benzonitrile

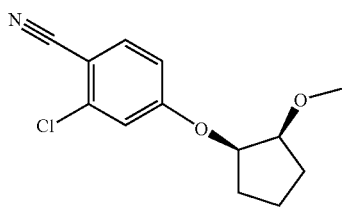

Step A: 2-Chloro-4-(cis-2-hydroxy-cyclopentyloxy)-benzonitrile

A 1.0 M solution of potassium t-butoxide in t-butanol (3.2 mL) was added to a 16 mL vial fitted with a septa cap containing 3 mL of dry THF and 300 mg (3 mmoles) of cis-1,2-dihydroxy cylcopentanol at 5° C. The mixture was stirred for 0.5 h at 5° C., after which time 3 mL of a 1.0 M THF solution of 4-fluoro-2-chloro-benzonitrile was added. The reaction was stirred at 5° C. for 3 h and then allowed to warm to room temperature and stirred overnight at room temperature. The reaction mixture was cooled to 0° C., poured into a seperatory funnel containing 15 mL of water, and extracted with 20 mL of methyl tert-butyl ether. The organic phase was washed with water, brine, dried (MgSO4), concentrated in vacuo, and the residue purified by reverse phase HPLC (Shimadzu) to give 185 mg 2-Chloro-4-(cis-2-hydroxy-cyclopentyloxy)-benzonitrile. GC/MS: 237 (M/Z for $C_{13}H_{14}ClNO$).

Step B: 2-Chloro-4-(cis-2-methoxy-cyclopentyloxy)-benzonitrile: 2-Chloro-4-(cis-2-hydroxy-cyclopentyloxy)-benzonitrile (76 mg, 0.32 mmol) was added to a flame dried round bottom flask under nitrogen containing 2 mL of dry DMF and 8.5 mg of 60% sodium hydride as an oil dispersion (0.35 mmol). The reaction was stirred at room temperature for 1 h, after which time methyl iodide (54 mg, 0.38 mmol) was added. The mixture was stirred for 16 h, quenched by the dropwise addition of 5 mL of water, and extracted with ether (2x). The combined organic phases were washed with brine, dried (MgSO4), concentrated and purified by reverse phase HPLC (Shimadzu) to give 35 mg of the title compound. GC/MS: 251 (M/Z for $C_{13}H_{14}ClNO_2$)—

Example 35

2-Chloro-4-(trans-2-methoxy-cyclopentyloxy)-benzonitrile

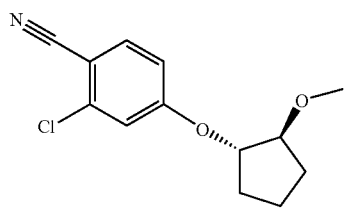

The title compound was prepared using the procedure described in Example 34 by using trans-1,2-dihydroxy cylcopentanol as the starting material to give 63 mg of the desired product. GC/MS: 251 (M/Z for $C_{13}H_{14}ClNO_2$).

Example 36

2-Chloro-4-(cis-2-methoxy-cyclohexyloxy)-benzonitrile

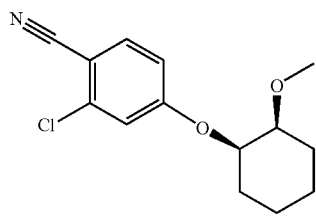

The title compound was prepared using the procedure described in Example 34 by using cis-1,2-dihydroxy-cylcohexanol as the starting alcohol to give 63 mg of the desired product. GC/MS: 265 (M/Z for $C_{14}H_{16}ClNO_2$).

Example 37

4-(cis-2-Allyloxy-cyclopentyloxy)-2-chloro-benzonitrile

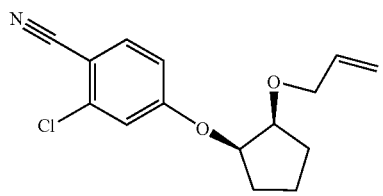

The product of Example 34, Step A (87 mg) was alkylated with allyl iodide (73.6 mg) according to the procedure of Example 34, Step B to give 12 mg of the title compound.
GC/MS: 277 (M/Z for $C_{15}H_{16}ClNO_2$).

Example 38

4-(trans-2-Allyloxy-cyclopentyloxy)-2-chloro-benzonitrile

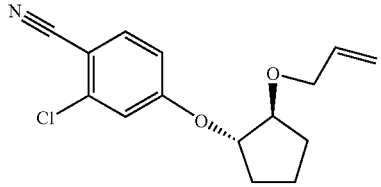

The title compound was prepared using the procedure described in Example 34 by using trans-1,2-dihydroxy cylcopentanol as the starting material followed by alkylation with allyl iodide to give 7.6 mg of the title compound. GC/MS: 277 (M/Z for $C_{15}H_{16}ClNO_2$).

Example 39

2-Chloro-4-(trans-2-methoxy-cyclohexyloxy)-benzonitrile

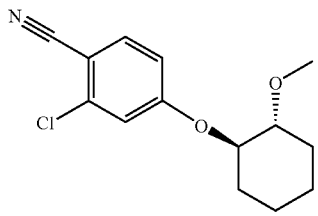

The title compound was prepared using the procedure described in Example 34 by using trans-1,2-dihydroxy-cylcohexanol as the starting alcohol to give 11 mg of the desired product. GC/MS: 265 (M/Z for $C_{14}H_{16}ClNO_2$).

Example 40

(1S,2R)-2-Chloro-4-(2-methyl-cyclohexyloxy)-benzonitrile

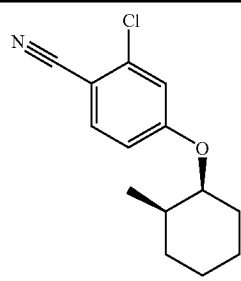

| Synthesis- | Method A |
| HPLC- | Method A |
| LCMS- | Method A |

MS: 250.23 (M+1 for $C_{14}H_{16}ClNO$); RT 3.47 min. Purity: 100.

Example 41

(1S,2S)-2-Chloro-4-(2-methyl-cyclohexyloxy)-benzonitrile

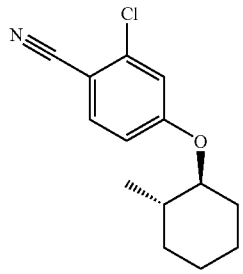

| Synthesis- | Method A |
| HPLC- | Method A |
| LCMS- | Method A |

MS: 250.24 (M+1 for $C_{14}H_{16}ClNO$); RT 3.44 min. Purity: 100.

Example 42

(1R,2R)-3-Chloro-4-(2-methyl-cyclohexyloxy)benzonitrile

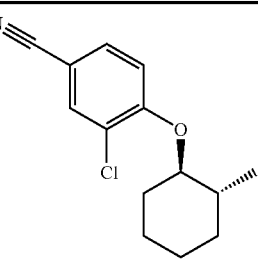

| Synthesis- | Method A |
| HPLC- | Method A |
| LCMS- | Method A |

MS: 250.24 (M+1 for $C_{14}H_{16}Cl NO$); RT 3.41 min. Purity: 100.

Example 43

3-Chloro-4-cycloheptyloxy-benzonitrile

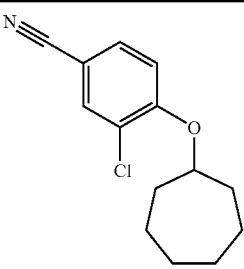

| Synthesis- | Method A |
| HPLC- | Method A |
| LCMS- | Method A |

MS: 250.24 (M+1 for $C_{14}H_{16}Cl NO$); RT 3.42 min. Purity: 100.

Example 44

3-Chloro-4-(3,3,5,5-tetramethyl-cyclohexyloxy)-benzonitrile

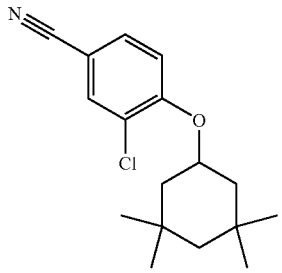

| Synthesis- | Method A |
| HPLC- | Method A |
| LCMS- | Method A |

MS: 292.29 (M+1 for $C_{17}H_{22}ClNO$); RT 3.87 min. Purity: 100.

Example 45

2-Chloro-4-cyclohexyloxy-benzonitrile

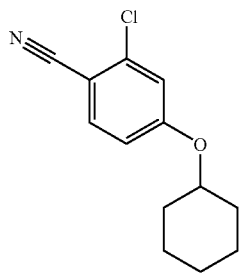

| Synthesis- | Method B |
| HPLC- | Method B |
| LCMS- | Method B |

MS: 236.2 (M+1 for $C_{13}H_{14}ClNO$); RT 4.28 min. Purity: 100.

Example 46

2-Chloro-4-cyclopentyloxy-benzonitrile

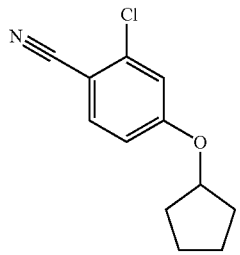

| Synthesis- | Method B |
| HPLC- | Method B |
| LCMS- | Method B |

MS: 222.2 (M+1 for $C_{12}H_{12}ClNO$); RT 4.04 min. Purity: 100.

Example 47

(1S,2R,5S)-2-Chloro-4-(2-isopropyl-5methyl-cyclohexyloxy)-benzonitrile

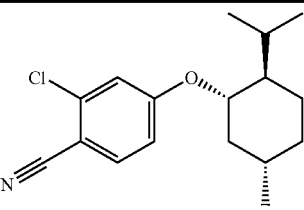

| Synthesis- | Method B |
| HPLC- | Method B |
| LCMS- | Method B |

MS: 292.28 (M+1 for $C_{17}H_{22}ClNO$); RT 4.82 min. Purity: 100.

Example 48

(1S,3R)-2-Chloro-4-(3-methyl-cyclohexyloxy)-benzonitrile

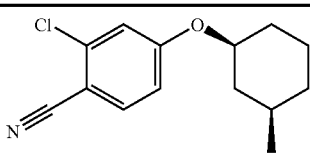

| Synthesis- | Method B |
| HPLC- | Method B |
| LCMS- | Method B |

MS: 250.24 (M+1 for $C_{14}H_{16}ClNO$); RT 4.34 min. Purity: 100.

Example 49

(1S,2S,5S)-2-Chloro-4-(5-isopropenyl-2-methyl-cyclohexyloxy)-benzonitrile

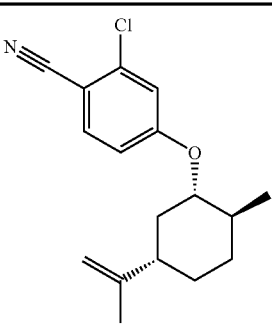

| Synthesis- | Method B |
| HPLC- | Method B |
| LCMS- | Method B |

MS: 290.31 (M+1 for $C_{17}H_{20}ClNO$); RT 4.56 min. Purity: 100.

Example 50
(1R,2S)-2-Chloro-4-(2-cyano-cyclohexyloxy)-benzonitrile

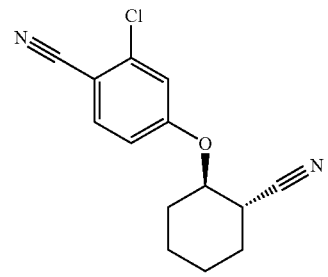

| Synthesis- | Method B |
| HPLC- | Method B |
| LCMS- | Method B |

MS: 261.2 (M+1 for $C_{14}H_{13}ClN_2O$); RT 3.61 min. Purity: 100.

Example 51
2-Chloro-4-(3,4-dimethyl-cyclohexyloxy)-benzonitrile

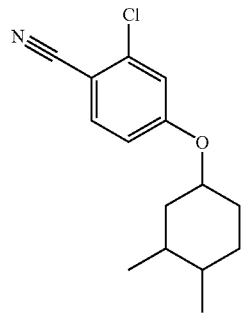

| Synthesis- | Method B |
| HPLC- | Method B |
| LCMS- | Method B |

MS: 264.25 (M+1 for $C_{15}H_{18}ClNO$); RT 4.46 min. Purity: 100.

Example 52
2-Chloro-4-(2,3-dimethyl-cyclohexyloxy)-benzonitrile

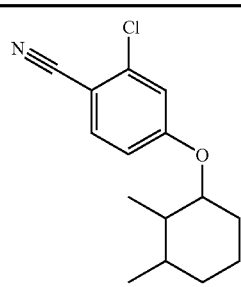

| Synthesis- | Method B |
| HPLC- | Method B |
| LCMS- | Method B |

MS: 264.25 (M+1 for $C_{15}H_{18}ClNO$); RT 4.49 min. Purity: 100.

Example 53
2-Chloro-4-(2,6-dimethyl-cyclohexyloxy)-benzonitrile

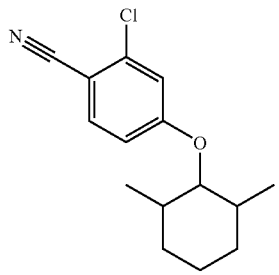

| Synthesis- | Method B |
| HPLC- | Method B |
| LCMS- | Method B |

MS: 264.27 (M+1 for $C_{15}H_{18}ClNO$); RT 4.51 min. Purity: 100.

Example 54
(1S,4S)-2-Chloro-4-(4-methyl-cyclohexyloxy)-benzonitrile

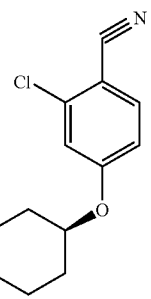

| Synthesis- | Method B |
| HPLC- | Method A |
| LCMS- | Method C |

MS: 250.24 (M+1 for $C_{14}H_{16}ClNO$); RT 2.42 min. Purity: 100.

Example 55

(1S,2R)-2-Chloro-4-(2-phenyl-cyclohexyloxy)-benzonitrile

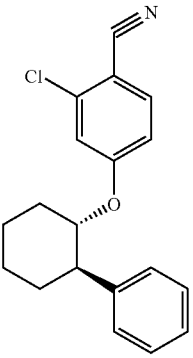

| Synthesis- | Method B |
|---|---|
| HPLC- | Method A |
| LCMS- | Method C |

MS: 312.29 (M+1 for $C_{19}H_{18}ClNO$); RT 2.41 min. Purity: 100.

Example 56

(1R,2R)-2-Chloro-4-(2-phenyl-cyclohexyloxy)-benzonitrile

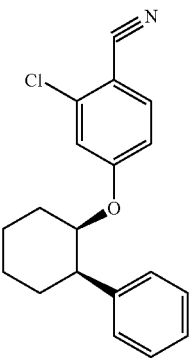

| Synthesis- | Method B |
|---|---|
| HPLC- | Method A |
| LCMS- | Method C |

MS: 312.28 (M+1 for $C_{19}H_{18}ClNO$); RT 2.42 min. Purity: 100.

Example 57

(1R,2R)-2-Chloro-4-(4-methyl-cyclohexyloxy)-benzonitrile

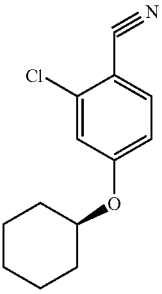

| Synthesis- | Method B |
|---|---|
| HPLC- | Method A |
| LCMS- | Method C |

MS: 250.2 (M+1 for $C_{14}H_{16}ClNO$); RT 2.48 min. Purity: 100.

Example 58

(1R,2S) 2-Chloro-4-(2-phenyl-cyclohexyloxy)-benzonitrile

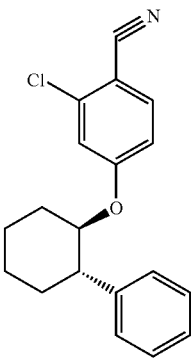

| Synthesis- | Method B |
|---|---|
| HPLC- | Method A |
| LCMS- | Method C |

MS: 312.29 (M+1 for $C_{19}H_{18}ClNO$); RT 2.44 min. Purity: 100.

Example 59

(1S,4R)-3-Chloro-4-(4-methyl-cyclohexyloxy)-benzonitrile

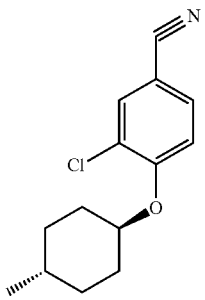

| Synthesis- | Method B |
| HPLC- | Method A |
| LCMS- | Method C |

MS: 250.29 (M+1 for $C_{14}H_{16}ClNO$); RT 2.39 min. Purity: 100.

Example 60

(1S,3R)₃-Chloro-4-(3-methyl-cyclohexyloxy)-benzonitrile

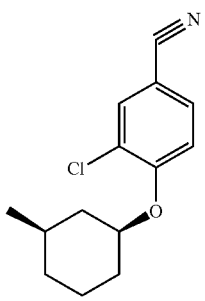

| Synthesis- | Method B |
| HPLC- | Method A |
| LCMS- | Method C |

MS: 250.29 (M+1 for $C_{14}H_{16}ClNO$); RT 2.39 min. Purity: 100.

Example 61

(1S,2R,5S)-3-Chloro-4-(2-isopropyl-5methyl-cyclohexyloxy)-benzonitrile

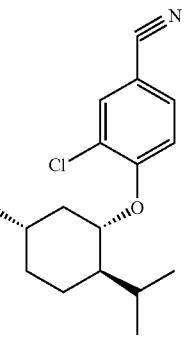

| Synthesis- | Method B |
| HPLC- | Method A |
| LCMS- | Method C |

MS: 292.29 (M+1 for $C_{17}H_{22}ClNO$); RT 2.52 min. Purity: 100.

Example 62

4-(Bicyclo[2.2.1]hept-2-yloxy)-2-chloro-benzonitrile

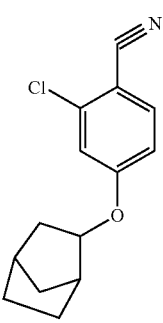

| Synthesis- | Method B |
| HPLC- | Method A |
| LCMS- | Method C |

MS: 248.21 (M+1 for $C_{14}H_{14}ClNO$); RT 2.36 min. Purity: 100.

Example 63

3-Chloro-4-(2,3-dimethyl-cyclohexyloxy)-benzonitrile

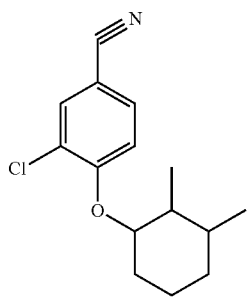

| Synthesis- | Method B |
| HPLC- | Method A |
| LCMS- | Method C |

MS: 264.28 (M+1 for $C_{15}H_{18}ClNO$); RT 2.46 min. Purity: 100.

Example 64

3-Chloro-4-(2,3-dimethyl-cyclohexyloxy)-benzonitrile

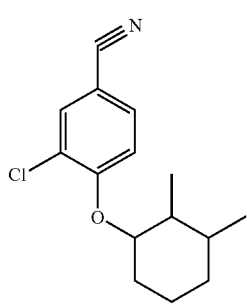

| Synthesis- | Method B |
| HPLC- | Method A |
| LCMS- | Method C |

MS: 264.23 (M+1 for $C_{15}H_{18}ClNO$); RT 2.53 min. Purity: 100.

* Example 64 is the same compound as the product of Example 63. It eluted as a separate fraction, fraction B, in the purification step. It was submitted for biological testing as a separate sample and thus is reported twice. Stereochemistry is unresolved.

Example 65

(3R,5R)-2-Chloro-4-(trans)-(3,5-dimethyl-cyclohexyloxy)-benzonitrile

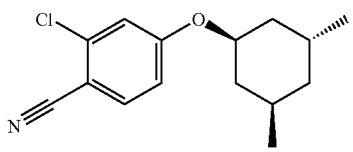

| Synthesis- | Method C |
| HPLC- | Method C |
| LCMS- | Method D |

MS: 264.21 (M+1 for $C_{15}H_{18}ClNO$); RT 3.57 min. Purity: 100.

Example 66

(1R,2R)-3-Chloro-4-(2-methyl-cyclopentyloxy)-benzonitrile

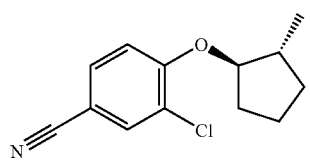

| Synthesis- | Method C |
| HPLC- | Method C |
| LCMS- | Method D |

MS: 236.2 (M+1 for $C_{13}H_{14}ClNO$); RT 3.41 min. Purity: 100.

Example 67

(1S,2S)-2-Chloro-4-(2-methyl-cyclopentyloxy)-benzonitrile

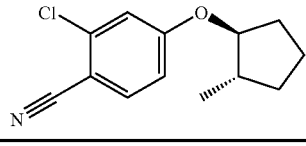

| Synthesis- | Method C |
| HPLC- | Method C |
| LCMS- | Method D |

MS: 224.13 (M+1 for $C_{13}H_{14}ClNO$); RT 3.42 min. Purity: 100.

Example 68

2-Chloro-4-cyclobutyloxy-benzonitrile

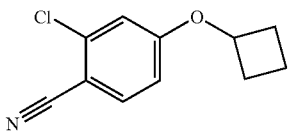

| Synthesis- | Method C |
| --- | --- |
| HPLC- | Method C |
| LCMS- | Method D |

MS: 208.16 (M+1 for $C_{11}H_{10}ClNO$); RT 3.22 min. Purity: 100.

Example 69

4-{[(1,2-cis)-2-ethoxycyclohexyl]oxy}-2-trifluoromethyl)benzonitrile

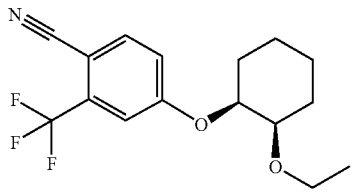

Cis-1,2-cyclohexanediol (10 g, 86.1 mmol), p-methoxybenzaldehyde dimethyl acetal (47.1 g, 258 mmol), p-toluenesulfonic acid (1.64 g, 8.61 mmol) and toluene (50 mL) was added to a 3-N 100 mL round bottom flask ("RBF") equipped with a dean-stark trap, $N^2$, and a temperature probe. The reaction was heated to reflux for 1 hour. The reaction was then cooled to 0° C. and diisobutylaluminum hydride (hereinafter "DIBAL-H") ((61.2 g, 430 mmol) was added slowly to the reaction. After all the DIBAL-H had been added the reaction was allowed to stir for 30 min. Then 175 mL of MeOH and 175 mL of aq. $NH_4Cl$ was added. The mixture was stirred for one hour during which time a solid formed. The solid was filtered off, and the remaining solution was added to ether (500 mL). The ether was then washed with brine (250 mL), dried and condensed. A column was run using 5:1 Hex:EA for 780 mL. A gradient was then passed through the column from 17%-80% EA for 800 mL. The desired fractions were collected and condensed. The resulting product (11.91 g, 58.54% yield) was combined with sodium hydride (2.688 g, 67.2 mmol) and 4-fluoro-2-(trifluoromethyl)benzonitrile (6.354 g, 33.60 mmol) in DMF (dimethylformamide) (100 mL). The reaction was heated to 70° C. for 24 hours. The reaction was extracted with EA (ethyl acetate) (250 mL) three times. The EA was washed with water (500 mL), sat. sodium bicarbonate (500 mL), and brine (500 mL). The EA layer was dried and condensed. The resulting oil was washed with 6 N (normal) NaOH (250 mL). It was then dried and condensed to give 4-[2-(4-methoxy-benzyloxy)cyclohexyloxy]-2-trifluoromethyl-benzonitrile (17.77 g with solvent in it, as a crude product.

2,3,-Dichloro-5,6-dicyano-1,4-benzoquinone (hereinafter "DDQ") (18.2 g, 80.2 mmol) was added to a solution of 4-[2-(4-methoxy-benzyloxy)cyclohexyloxy]-2-trifluoromethyl-benzonitrile (17.77 g, 43.83 mmol), methylene chloride (500 mL) and water (50 mL). The reaction was allowed to stir at room temperature for 3 days. A solid formed and was filtered off. The resulting filtrate was passed through a silica plug and condensed under reduced pressure. A column was run using a gradient of 17-80% EA in Hexanes. A second column was run using 4:1 Hex:EA. This yielded the desired product, 4-(2-hydroxy-cyclohexyloxy)-2-trifluoromethyl-benzonitrile (4.0 g, 32% yield).

Sodium hydride (0.014 g, 0.351 mmol) was cooled to 0° C. 4-(2-Hydroxy-cyclohexyloxy)-2-trifluoromethyl-benzonitrile (0.1 g, 0.351 mmol) was then added and the two reagents were allowed to stir for 5 minutes. Iodoethane (0.547 g, 3.51 mmol) was then added and the reaction was allowed to warm to room temp and stir overnight under nitrogen. Water (250 mL) was added and the reaction was extracted into EA (700 mL). The EA was washed with sodium bicarbonate (500 mL) and brine (250 mL). The EA layer was dried and condensed to give crude product. The compound was placed on a column and then hexane was run through. After which time 0-20% EA was washed through, after which 300 mL of 20% EA was washed through. The clean fractions were collected and condensed yielding 4-{[(1,2-cis)-2-ethoxycyclohexyl]oxy}-2-trifluoromethyl)benzonitrile (0.0251 g, 22.85% yield). $^1$HNMR (400 MHz, Chloroform-D) ppm 1.14 (t, J=6.95 Hz, 3H) 1.40 (m, 2H) 1.53 (s, 1H) 1.60 (m, 2H) 1.74 (s, 2H) 1.87 (m, 1H) 2.03 (m, 1H) 3.50 (m, J=13.24, 13.24, 6.83, 2.81 Hz, 2H) 4.64 (s, 1H) 7.15 (dd, J=8.66, 2.56 Hz, 1H) 7.35 (d, J=2.68 Hz, 1H) 7.71 (d, J=9.03 Hz, 1H)

Example 70

4-{[(1,2-trans)-2-methoxycyclohexyl]oxy}-2-trifluoromethyl)benzonitrile

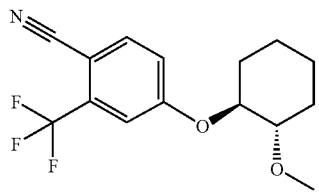

Cyclohexene oxide (13.11 g, 133.6 mmol), 4-fluoro-2-(trifluoromethyl)benzonitrile (5.00 g, 26.72 mmol), and potassium carbonate (5.539 g, 40.08 mmol) in DMF (dimethylformamide) (50 mL) were heated to 95° C. for 14 hours. The reaction was then allowed to cool. The reaction was added to water (300 mL) and then extracted with ethyl acetate (200 mL) three times. The combined extracts were washed with water (300 mL), 0.5M NaOH (300 mL), water (300 mL), and a 15% sodium chloride solution (300 mL). The organic phase was dried over sodium sulfate, filtered and evaporated.

The crude material was purified by chromatography on silica, eluting with a 2:1 solution of hexane:ethyl acetate. This yielded the desired product, 4-(2-hydroxy-cyclohexyloxy)-2-trifluoromethyl-benzonitrile (3.8 g, 50% yield).

A suspension of sodium hydride (0.01402 g, 0.351 mmol) in DMF (50 mL) was cooled to 0° C. and 4-(2-hydroxy-cyclohexyloxy)-2-trifluoromethyl-benzonitrile (0.100 g, 0.351 mmol) was added. After 5 minutes, iodomethane (0.498 g, 3.51 mmol) was added and the reaction was allowed to warm to room temperature and stir overnight under nitrogen. Water (250 mL) was then added and the reaction was extracted into EA (ethylacetate) (500 mL). The EA was washed with sodium bicarbonate (250 mL), and brine (250 mL). The EA layer was dried and condensed to give crude product. The compound was placed on a column and then hexane was run through. After which time the eluting mixture was changed to 10:1 hexane:ethyl acetate. The desired fractions were collected and condensed yielding the desired product 4-{[(1,2-trans)-2-methoxycyclohexyl]oxy}-2-trifluoromethyl)benzonitrile. (0.048 g, 46% yield). $^1$H NMR (400 MHz, Chloroform-D) ppm 1.34 (m, 3H) 1.49 (m, 1H) 1.75 (m, 2H) 2.05 (m, 1H) 2.14 (m, 1H) 3.29 (m, J=7.87, 4.73, 4.73, 4.39 Hz, 1H) 3.36 (s, 3H) 4.25 (ddd, J=10.00, 7.81, 4.39 Hz, 1H) 7.17 (dd, J=8.54, 2.68 Hz, 1H) 7.31 (d, J=2.44 Hz, 1H) 7.70 (dd, J=8.54, 0.49 Hz, 1H).

Example 71

(1S,2S)-4-(2-Allyloxy-cyclohexyloxy)-2-trifluoromethyl-benzonitrile

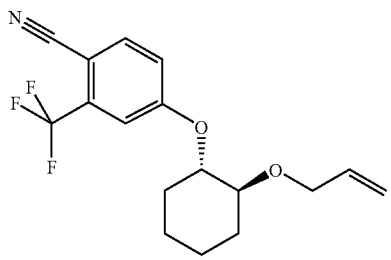

To 15 mL anhydrous DMF (dimethylformamide) was added trans 2-allyloxy-cyclohexanol (1.144 g, 7.323 mmol), then NaH (60% in oil, 0.4261 g, 10.65 mmol) was added and stirred at room temperature 15 min. Then 4-fluoro-2-trifluoromethyl benzonitrile (1.435 g, 7.59 mmol) was added, and the solution was stirred at room temperature overnight. The DMF solution was extracted twice with hexane. Then the reaction mixture was poured into 100 mL of water and extracted three times with ether. The combined ether layers were extracted three times with water, then once with brine, and dried over magnesium sulfate, filtered, and the solvent removed. The crude product was chromatographed with a hexane/methylene chloride mixture (100% hexane to 1:1 hexane/methylene chloride). The desired fractions were combined, and the solvent removed to give 0.6245 g product. HNMR (CDCl$_3$, ppm) 7.70-7.68 (1H, d, J=8.8 Hz), 7.32 (1H, s), 7.19-7.16 (1H, d, J=8.8 Hz), 5.80-5.71 (1H, m), 5.20-5.0 (2H, m), 4.30-4.20 (1H, m), 4.10-4.00 (1H, m) 4.00-3.90 (1H, m), 3.50-3.39 (1H, m), 2.20-2.00 (2H, m), 1.80-1.70 (2H, m), 1.65-1.20 (5H, m). FNMR (CDCl$_3$)-62.67 ppm. MS+326.

Example 72

(trans)-(−)-4-(2-Cyano-cyclohexyloxy)-2-trifluoromethyl-benzonitrile

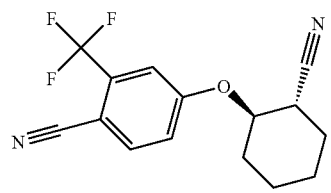

(trans)-4-(2-Cyano-cyclohexyloxy)-2-trifluoromethyl-benzonitrile was separated by chiral HPLC to obtain (trans)-(−)-4-(2-Cyano-cyclohexyloxy)-2-trifluoromethyl-benzonitrile (peak 2, retention time 22.3 minutes) [a]24.3° C.=−65.6°

Example 73

(trans)-(+)-4-(2-Cyano-cyclohexyloxy)-2-trifluoromethyl-benzonitrile

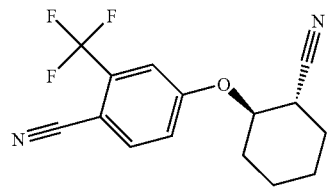

Sodium hydride (2.5 g) was added to 100 ml of THF and cooled to −78° C., then trans-2-nitrile-1-hydroxy-cyclohexane (7.3 g) was added. The mixture was stirred for 5 minutes. Afterwards, 4-fluoro-3-trifluoromethyl-4-cyano-benzene (10 g, in THF) was then added drop wise. The reaction was stirred overnight and allowed to warm up naturally. The reaction mixture was dissolved in ethyl acetate (EtOAc) (300 ml) and washed with 2×100 ml of water; and 1×100 ml of brine. The organic layer was dried over MgSO and concentrated. The residue was chromatographed using 4:1 hexane:CH$_2$Cl$_2$ to 1:1 hexane:CH$_2$Cl$_2$ to yield a clear oil as the desired product (6.9 g) MS 300 (for M+1).

This trans residue was separated by chiral HPLC to obtain (trans)-(+)-4-(2-Cyano-cyclohexyloxy)-2-trifluoromethyl-benzonitrile (peak 1, retention time 18 minutes, 2.2 g) [a]24.3° C.=65.2°

Example 74

(1R,3R)-2-Chloro-4-(3-hydroxy-cyclohexyloxy)-benzonitrile

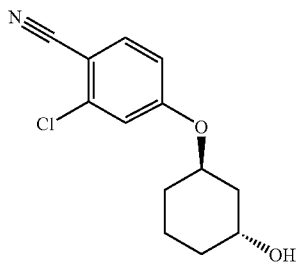

A commercial mixture of cis/trans 1,3-cyclohexanediol (7.77 g, 66.9 mmol) was dissolved in 50 mL anhydrous THF (tetrahydrofuran), under a nitrogen atmosphere, and cooled in an ice/acetone bath. NaH (60% suspension in oil, 2.69 g, 6.725 mmol) was then added and the solution stirred approximately 10 min. Then a solution of 2-chloro-4-fluorobenzonitrile (1.06 gms, 6.79 mmol)(in 20 mL anhydrous THF was added in a slow, steady stream (not dropwise). The cold bath was removed, and allowed to stir at room temperature overnight. The reaction was quenched with approximately 10 mL 5% citric acid and the THF was removed by rotovap. off. Ethyl acetate was added and the layers were separated. The aqueous layer was extracted twice more with ethyl acetate and the organic layers were combined. The combined organic layers were washed twice with brine, then dried over magnesium sulfate, filtered and rotovapped. The resulting product was triturated with hexane, and the hexane decanted off. The crude product was chromatographed with an ethyl acetate hexane gradient (10% ethyl acetate to 50% ethyl acetate), and the desired fractions were combined, and the solvent removed. The results of two such runs were combined, and submitted for preparative reverse phase HPLC. The title compound (0.1575 g) was returned. HNMR (CDCl$_3$, ppm) 7.5 (1H, d, J=8.8 Hz), 6.96 (1H, s), 6.82 (1H, d, J=8.8 Hz), 4.8-4.6 (1H, m), 4.2-4.1 (1H, m), 2.1-1.4 (9H, m).

Example 75

The compounds of Formula I have affinity for the androgen receptor. This affinity has been demonstrated for selected compounds using the human receptor. The description below describes how the assay was carried out.

Competitive binding analysis was performed on baculovirus/Sf9 generated hAR extracts in the presence or absence of different concentrations of test agent and a fixed concentration of $^3$H-dihydrotestosterone ($^3$H-DHT) as tracer. This binding assay method is a modification of a protocol previously described (Liao S., et. al. *J. Steroid Biochem.* 20:11-17 1984). Briefly, progressively decreasing concentrations of compounds are incubated in the presence of hAR extract (Chang et al. *P.N.A.S.* Vol. 89, pp. 5546-5950, 1992), hydroxylapatite, and 1 nM $^3$H-DHT for one hour at 4° C. Subsequently, the binding reactions are washed three times to completely remove excess unbound $^3$H-DHT. hAR bound $^3$H-DHT levels are determined in the presence of compounds (i.e. competitive binding) and compared to levels bound when no competitor is present (i.e. maximum binding). Compound binding affinity to the hAR is expressed as the concentration of compound at which one half of the maximum binding is inhibited. Table I below provides the results that were obtained for selected compounds (reported data is the mean of multiple tests as shown below)

| Example # | Structure | AR Binding IC$_{50}$ (nM) |
|---|---|---|
| 1 | 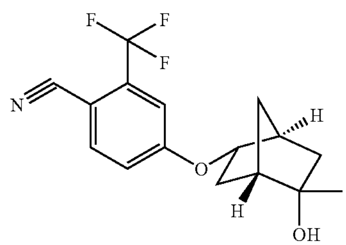 | 655 (N = 8) |
| 2 | 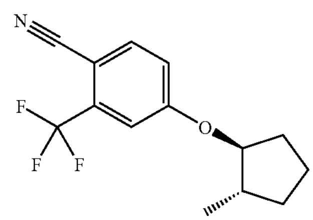 | 153 (a) |
| 3 | 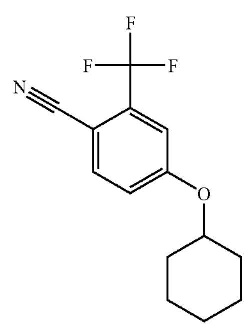 | 73 (a) |
| 4 | 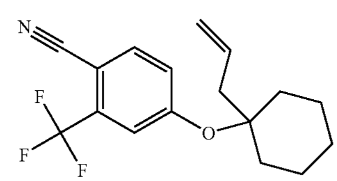 | 48 (a) |
| 5 | 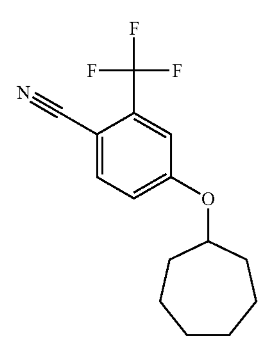 | 319 (N = 6) |

-continued

| Example # | Structure | AR Binding IC$_{50}$ (nM) |
|---|---|---|
| 6 | 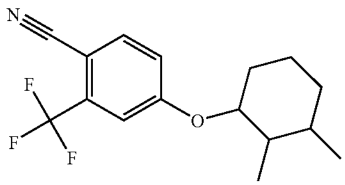 | 356 (a) |
| 7 | 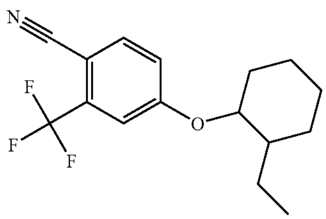 | 125 (a) |
| 8 | 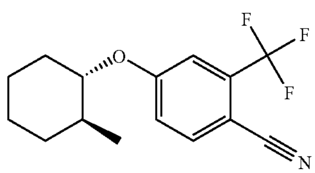 | 106 (a) |
| 9 | Chiral | 22 (a) |
| 10 | 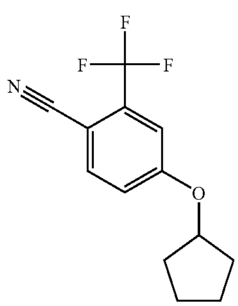 | 156 (a) |
| 11 | 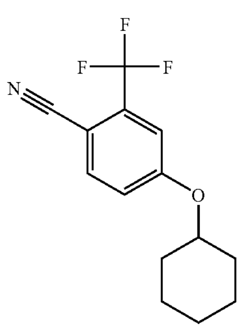 | 390 (N = 12) |
| 12 | | 73 (a) |
| 13 | Chiral | 102 (a) |
| 14 | Chiral | 58 (N = 8) |
| 15 | | 243 (a) |

-continued

| Example # | Structure | AR Binding IC$_{50}$ (nM) |
|---|---|---|
| 16 | 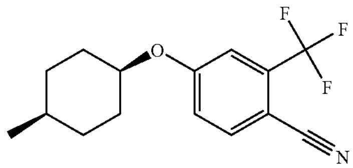 | 479 (a) |
| 17 | 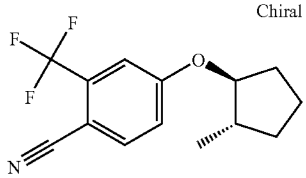 | 252 (a) Chiral |
| 18 | 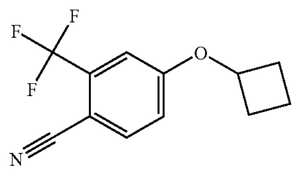 | 466 (a) |
| 19 | 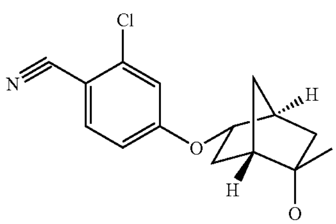 | 9 (a) |
| 20 | 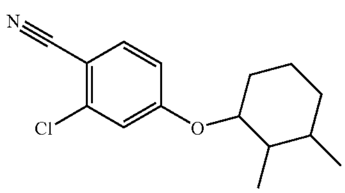 | 227 (a) |
| 21 | 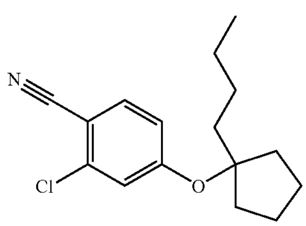 | 206 (a) |
| 22 | 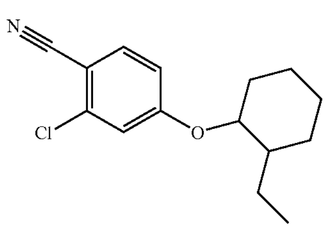 | 71 (a) |
| 23 | | 145 (a) |
| 24 | | 106 (a) |
| 25 | | 82 (a) |
| 26 | | 404 (N = 6) |
| 27 | | 30 (a) |
| 28 | | 49 (a) |

-continued

| Example # | Structure | AR Binding IC$_{50}$ (nM) |
|---|---|---|
| 29 | 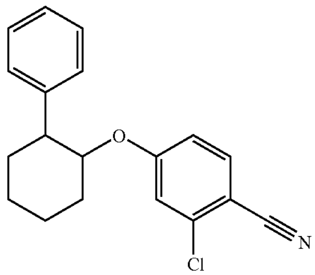 | 89 (a) |
| 30 | 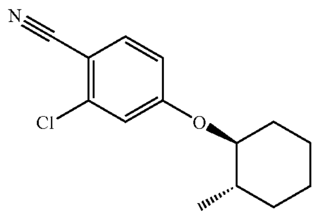 | 24 (a) |
| 31 | 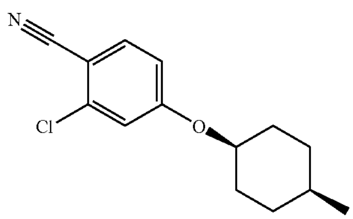 | 212 (a) |
| 32 | 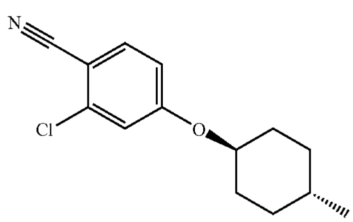 | 164 (a) |
| 33 | 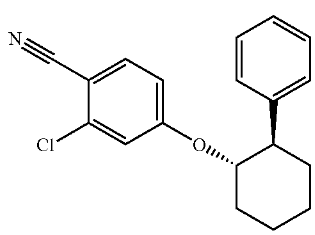 | 60 (a) |
| 34 | 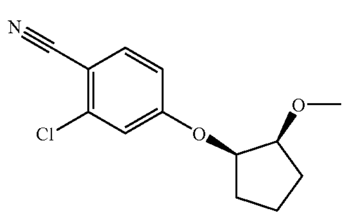 | 172 (a) |
| 35 | | 97 (a) |
| 36 | | 123 (a) |
| 37 | | 134 (a) |
| 38 | | 120 (a) |
| 39 | | 76 (a) |
| 40 | Chiral | 31 (a) |

| Example # | Structure | AR Binding IC$_{50}$ (nM) |
|---|---|---|
| 41 | Chiral | 18 (a) |
| 42 | Chiral | 343 (a) |
| 43 | 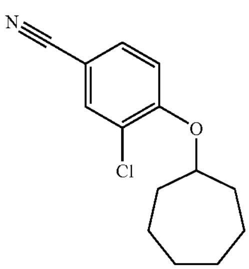 | 289 (N = 6) |
| 44 | 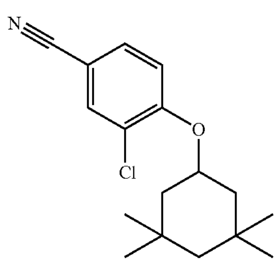 | 410 (a) |
| 45 | 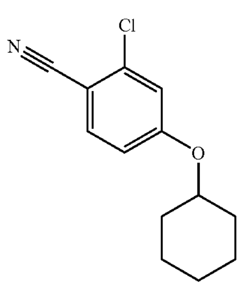 | 196 (a) |
| 46 | | 49 (a) |
| 47 | Chiral | 107 (a) |
| 48 | Chiral | 218 (a) |
| 49 | Chiral | 10 (a) |
| 50 | Chiral | 17 (a) |

-continued
| Example # | Structure | AR Binding IC$_{50}$ (nM) |
|---|---|---|
| 51 | 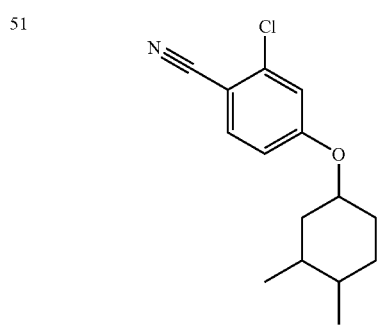 | 442 (a) |
| 52 | 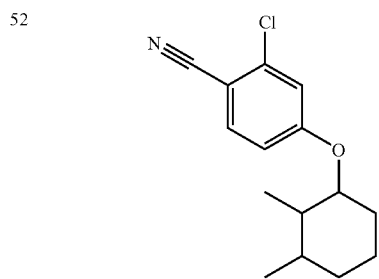 | 72 (a) |
| 53 | 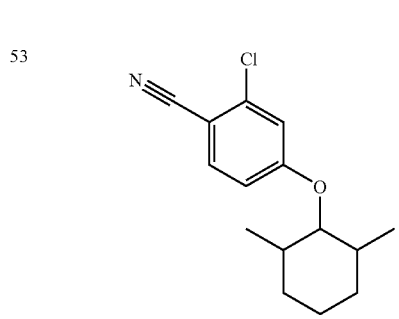 | 33 (a) |
| 54 | 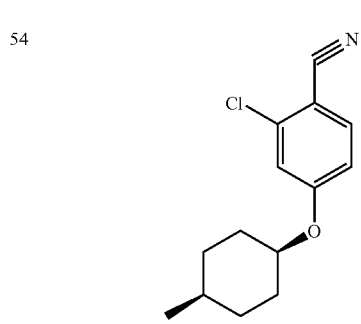 | 356 (a) |
-continued
| Example # | Structure | AR Binding IC$_{50}$ (nM) |
|---|---|---|
| 55 | Chiral 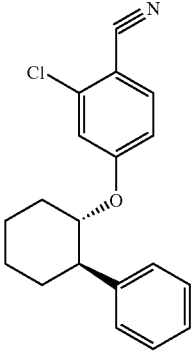 | 265 (c) |
| 56 | Chiral 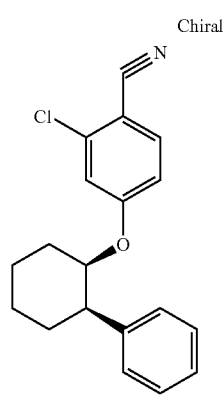 | 366 (a) |
| 57 | 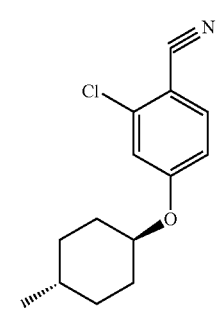 | 137 (a) |
| 58 | Chiral 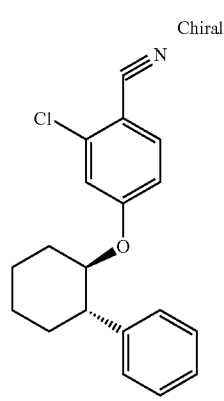 | 278 (a) |

-continued
| Example # | Structure | AR Binding IC$_{50}$ (nM) |
|---|---|---|
| 59 | 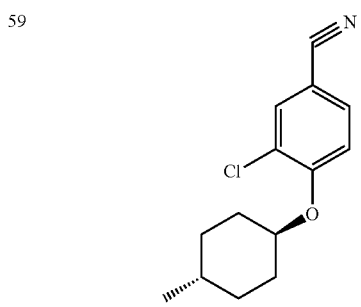 | 341 (a) |
| 60 | 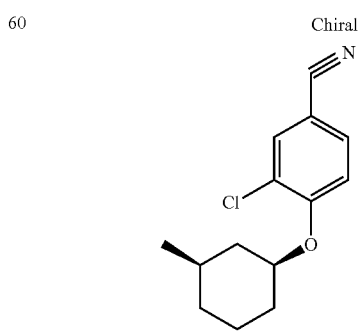 Chiral | 388 (a) |
| 61 | 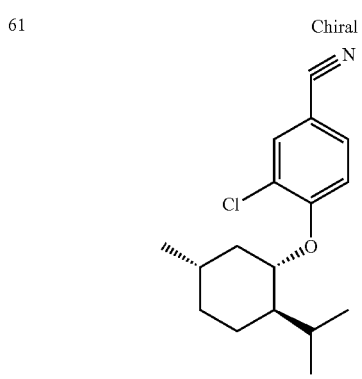 Chiral | 257 (a) |
| 62 | 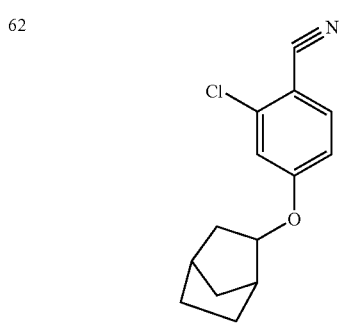 | 46 (a) |
-continued
| Example # | Structure | AR Binding IC$_{50}$ (nM) |
|---|---|---|
| 63 | 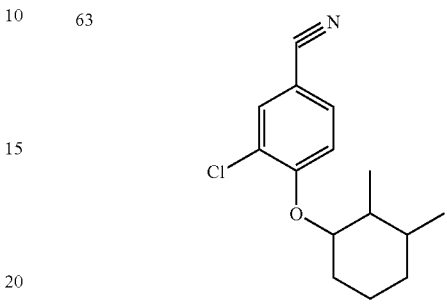 | 374 (a) |
| 64 | 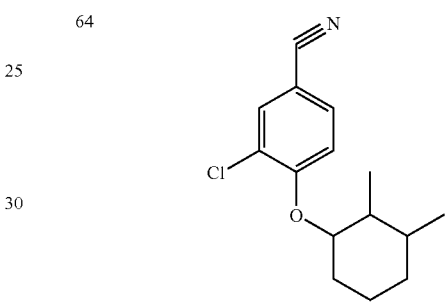 | 119 (A) |
| 65 | 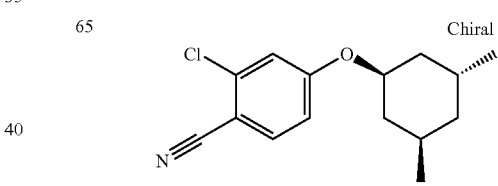 Chiral | 437 (a) |
| 66 | 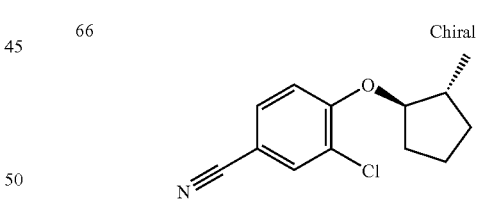 Chiral | 402 (a) |
| 67 | 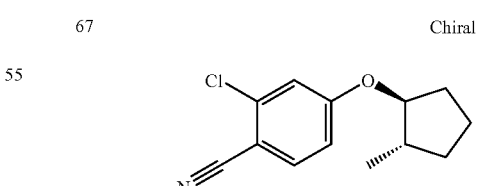 Chiral | 44 (a) |
| 68 | 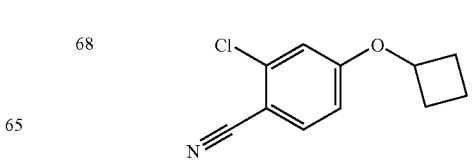 | 297 (c) |

-continued

| Example # | Structure | AR Binding IC$_{50}$ (nM) |
|---|---|---|
| 69 | [structure: 4-cyano-3-trifluoromethylphenyl ether of cyclohexane bearing ethoxy group] | 281 (a) |
| 70 | [structure: 4-cyano-3-trifluoromethylphenyl ether of cyclohexane bearing methoxy group] | 158 (c) |
| 71 | [structure: 4-cyano-3-trifluoromethylphenyl ether of cyclohexane bearing allyloxy group] | 374 (c) |
| 72 | [structure: 4-cyano-3-trifluoromethylphenyl ether of cyclohexane bearing CN; (trans)-(−)] | 43 |
| 73 | [structure: 4-cyano-3-trifluoromethylphenyl ether of cyclohexane bearing CN; trans(+)] | 61 |

-continued

| Example # | Structure | AR Binding IC$_{50}$ (nM) |
|---|---|---|
| 74 | [structure: 4-cyano-3-trifluoromethylphenyl ether of cyclohexane bearing OH] | UA | a—mean of 2 tests
b—mean of 3 tests
c—mean of 4 tests
ND—not determined
UA—unavailable Example 76

The compounds ability to antagonize the effects of androgen on the androgen receptor were determined in a whole cell assay as described immediately below.

Experimental Procedure for AR Antagonist Cell Assay

Cell line: MDA-MB453-MMTV clone 54-19. This cell line is a stable transfected cell line with MDA-MB453 cell background (a human breast tumor cell line expressing androgen receptor). A MMTV minimal promoter containing ARE was first cloned in front of a firefly luciferase reporter gene. Then the cascade was cloned into transfection vector pUV120puro. Electroporation method was used for transfecting MDA-MB-453 cell. Puromycin resistant stable cell line was selected.

Cell Culture Media and Reagents:

Culture medium: DMEM (high glucose, Gibco cat #: 11960-044), 10% FBS, and 1% L-glutamine Plating medium: DMEM (phenol red free), 10% charcoal treated HyClone serum, 1% L-glutamine Assay medium: DMEM (phenol red free), 1% charcoal treated HyClone serum, 1% L-glutamine, and 1% penicillin/streptomycin 3× luciferase buffer: 2% beta-mercaptoethanol, 0.6% ATP, 0.0135% luciferine in cell lysis buffer Assay Procedure:
1. Cells are maintained in culture medium, splitting cells when they reach 80-90% confluence
2. To test compounds, 10,000 cells/well are plated to opaque 96 cell culture plate in 100 ul/well plating medium, culture for overnight at 37° C. in cell culture incubator
3. Carefully remove plating medium, then add 80 ul/well of pre-warmed assay medium, add 10 ul/well testing compound (final concentration at) 1000 nM, 200 nM, 40 nM, 8 nM, 1.6 nM, and 0.32 nM), incubate at 37° C. for 30 minutes
4. Add 10 ul/well freshly prepared DHT (final concentration at 100 pM) to each well, incubate at 37° C. for 17 hr (overnight)
5. Add 50 ul/well 3× luciferase buffer, incubate at room temperature for 5 minutes, then count on Luminometer The fold induction over background by 100 pM DHT in the absence of testing compounds is standardized as 100% and experimental result is expressed as percentage of inhibition by testing compounds.

The results are described below in Table III. The results are reported as the mean of multiple tests as described below (the numbers of tests are indicated in the footnote). N.D. denotes that the compound was not tested.

| Example # | Structure | AR Cell IC$_{50}$ (nM) |
|---|---|---|
| 1 | 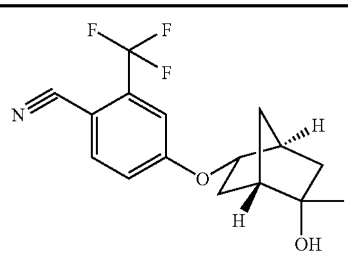 | 80 (c) |
| 2 | 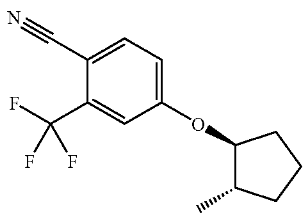 | ND |
| 3 | 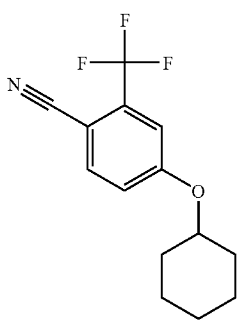 | >1000 (a) |
| 4 | 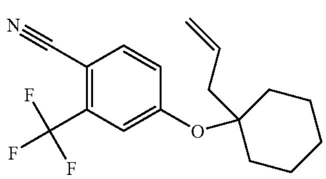 | >1000 (a) |
| 5 | 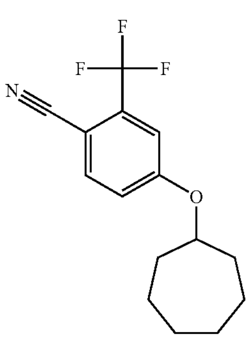 | ND |

-continued

| Example # | Structure | AR Cell IC$_{50}$ (nM) |
|---|---|---|
| 6 | 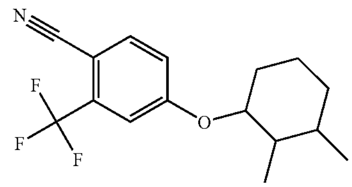 | ND |
| 7 | 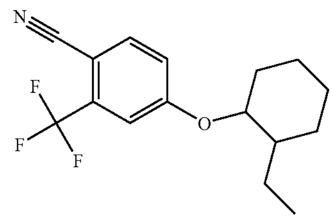 | 329 (a) |
| 8 | 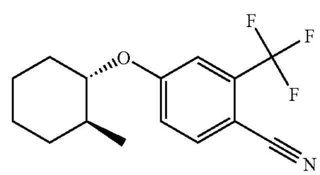 | 494 (a) |
| 9 | 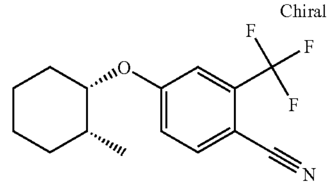 | 751 (a) |
| 10 | 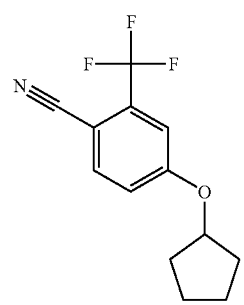 | 605 (a) |
| 11 | 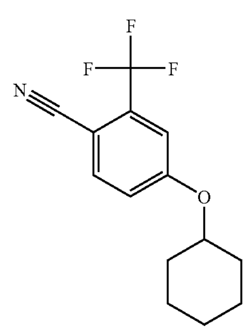 | 0.5 (a) |

-continued

| Example # | Structure | AR Cell IC$_{50}$ (nM) |
|---|---|---|
| 12 | | >1000 (a) |
| 13 | Chiral | N.D. |
| 14 | Chiral | 13 (N = 8) |
| 15 | | N.D. |
| 16 | 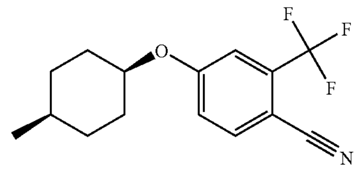 | ND |
| 17 | Chiral | ND |
| 18 | 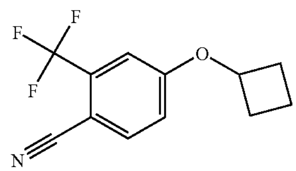 | ND |
| 19 | 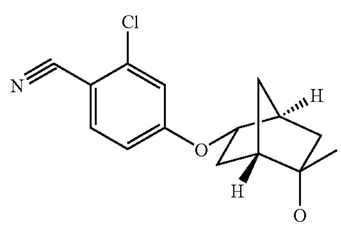 | 14 (a) |
| 20 | 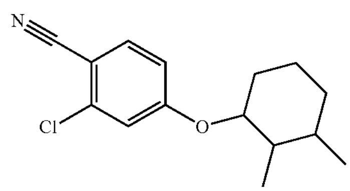 | ND |
| 21 | 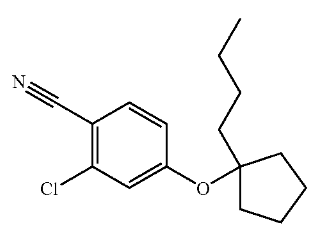 | >1000 (a) |
| 22 | 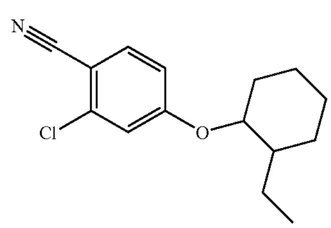 | >1000 (a) |

-continued

| Example # | Structure | AR Cell IC$_{50}$ (nM) |
|---|---|---|
| 23 | 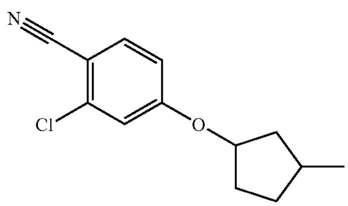 | 202 (a) |
| 24 | 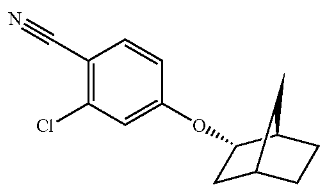 | 15 (a) |
| 25 | 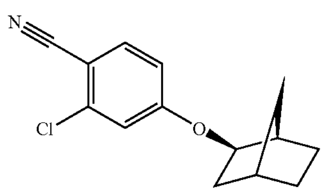 | <0.32 (a) |
| 26 | 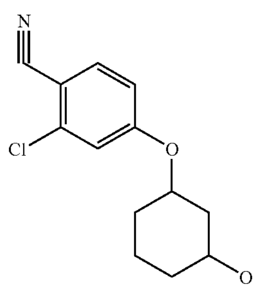 | 46 (a) |
| 27 | 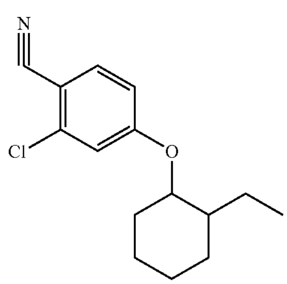 | 330 (a) |
| 28 | 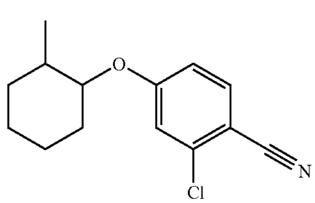 | ND |

-continued

| Example # | Structure | AR Cell IC$_{50}$ (nM) |
|---|---|---|
| 29 | | ND |
| 30 | | ND |
| 31 | | 66 (N = 1) |
| 32 | | 740 (N = 1) |
| 33 | | 485 (N = 1) |
| 34 | | 340 (a) |

-continued

| Example # | Structure | AR Cell IC$_{50}$ (nM) |
|---|---|---|
| 35 | 2-chloro-4-((1R,2S)-2-methoxycyclopentyloxy)benzonitrile | ND |
| 36 | 2-chloro-4-((1S,2S)-2-methoxycyclohexyloxy)benzonitrile | 300 (a) |
| 37 | 4-((1R,2S)-2-(allyloxy)cyclopentyloxy)-2-chlorobenzonitrile | ND |
| 38 | 4-((1S,2R)-2-(allyloxy)cyclopentyloxy)-2-chlorobenzonitrile | N.D. |
| 39 | 2-chloro-4-((1R,2R)-2-methoxycyclohexyloxy)benzonitrile | ND |
| 40 | Chiral — 2-chloro-4-((1S,2R)-2-methylcyclohexyloxy)benzonitrile | 114 (a) |

-continued

| Example # | Structure | AR Cell IC$_{50}$ (nM) |
|---|---|---|
| 41 | Chiral — 2-chloro-4-((1R,2S)-2-methylcyclohexyloxy)benzonitrile | 46 (a) |
| 42 | Chiral — 3-chloro-4-((1R,2S)-2-methylcyclohexyloxy)benzonitrile | N.D. |
| 43 | 3-chloro-4-(cycloheptyloxy)benzonitrile | 12 (c) |
| 44 | 3-chloro-4-(3,3,5,5-tetramethylcyclohexyloxy)benzonitrile | N.D. |
| 45 | 2-chloro-4-(cyclohexyloxy)benzonitrile | 147 (a) |

-continued
| Example # | Structure | AR Cell IC$_{50}$ (nM) |
|---|---|---|
| 46 | 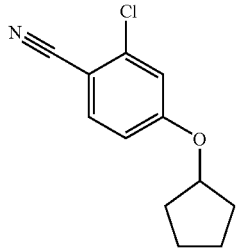 | 18 (a) |
| 47 | 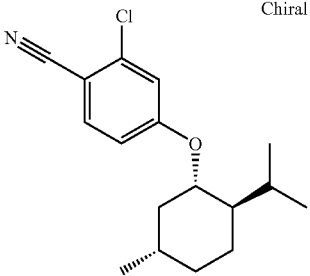 Chiral | 750 (a) |
| 48 | 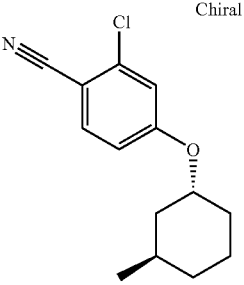 Chiral | ND |
| 49 | 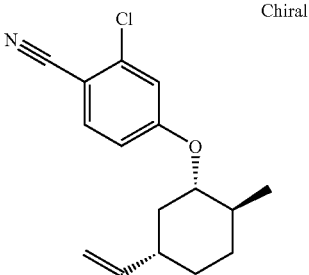 Chiral | 49 (a) |
| 50 | 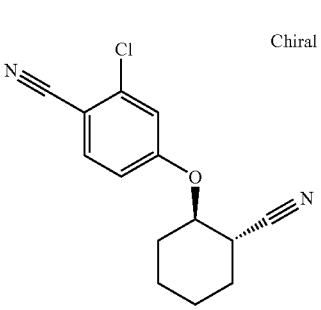 Chiral | 202 (a) |
-continued
| Example # | Structure | AR Cell IC$_{50}$ (nM) |
|---|---|---|
| 51 | 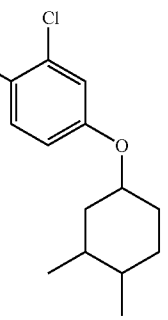 | N.D. |
| 52 | 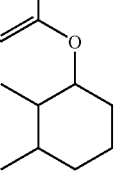 | 308 (a) |
| 53 | 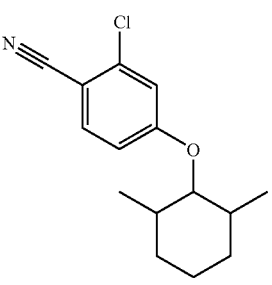 | >1000 (a) |
| 54 | 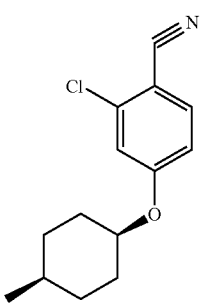 | N.D. |

-continued

| Example # | Structure | AR Cell IC$_{50}$ (nM) |
|---|---|---|
| 55 | Chiral | 421 (a) |
| 56 | Chiral | N.D. |
| 57 | 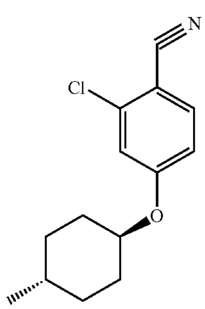 | 8 (a) |
| 58 | Chiral | N.D. |
| 59 |  | N.D. |
| 60 | Chiral | N.D. |
| 61 | Chiral | N.D. |
| 62 |  | <0.32 (a) |

-continued

| Example # | Structure | AR Cell IC$_{50}$ (nM) |
|---|---|---|
| 63 | 3-chloro-4-((2,3-dimethylcyclohexyl)oxy)benzonitrile | N.D. |
| 64 | 3-chloro-4-((2,3-dimethylcyclohexyl)oxy)benzonitrile | 217 (a) |
| 65 | 2-chloro-4-((3,5-dimethylcyclohexyl)oxy)benzonitrile, Chiral | N.D. |
| 66 | 2-chloro-4-((2-methylcyclopentyl)oxy)benzonitrile, Chiral | N.D. |
| 67 | 2-chloro-4-((2-methylcyclopentyl)oxy)benzonitrile, Chiral | <0.32 (a) |
| 68 | 2-chloro-4-cyclobutoxybenzonitrile | 103 (a) |
| 69 | 4-((2-ethoxycyclohexyl)oxy)-2-(trifluoromethyl)benzonitrile | ND |

-continued

| Example # | Structure | AR Cell IC$_{50}$ (nM) |
|---|---|---|
| 70 | 4-((2-methoxycyclohexyl)oxy)-2-(trifluoromethyl)benzonitrile | 10 (a) |
| 71 | 4-((2-(allyloxy)cyclohexyl)oxy)-2-(trifluoromethyl)benzonitrile | 23 (a) |
| 72 | 4-((2-cyanocyclohexyl)oxy)-2-(trifluoromethyl)benzonitrile (trans)-(−) | 12 (c) |
| 73 | 4-((2-cyanocyclohexyl)oxy)-2-(trifluoromethyl)benzonitrile trans(+) | 196 (c) |
| 74 | 4-((3-hydroxycyclohexyl)oxy)-2-(trifluoromethyl)benzonitrile | UA | a—mean of 2 tests
b—mean of 3 tests
c—mean of 4 tests
ND—not determined
UA—Unavailable

Example 77

Animal Model for Inhibition of Sebum Production

Luderschmidt et al describes an animal model for testing whether compounds are capable of modulating sebum secretion. Arch. Derm. Res. 258, 185-191 (1977). This model uses male Syrian hamsters, whose ears contain sebaceous glands. The product of Example 14 was screened in this model.

Testing for sebum inhibition was carried out in the following manner. Male Syrian hamsters aged 9 to 10 weeks were introduced into the laboratory environment and acclimated for 2 weeks prior to use in the study. Each group consisted of 5 animals and run in parallel with vehicle and positive controls. Prior to administration, a sufficient quantity each compound was dissolved in 1 mL of a solvent consisting of ethanol, and propylene glycol (70/30% v/v) to achieve a final concentration of 3.0 w/v %.

Animals were dosed topically twice daily, five days a week, for 4 weeks. Each dose consisted of 25 micro liters of vehicle control or drug. The dose was applied to the ventral surfaces of both the right and left ears. All animals were sacrificed approximately 18-24 hours after the final dose. The right ears were collected from each animal and used for sebum analysis.

The ears were prepped for HPLC analysis in the following manner. One 8 mm distal biopsy punch was taken, just above the anatomical "V" mark in the ear to normalize the sample area. The punch was pulled apart. The ventral biopsy surface (the area where the topical dose was directly applied to the sebaceous glands) was retained for testing and the dorsal surface of the biopsy punch was discarded.

Tissue samples were blown with $N_2$ gas and stored at $-80°$ C. under nitrogen until HPLC analysis. In addition to ear samples, an aliquot of each drug and vehicle (at least 250 ul) was also stored at $-80°$ C. for inclusion in the HPLC analysis.

HPLC analysis was carried out on an extract of the tissue sample. Tissue samples were contacted with 3 ml of solvent (a 4:1 admixture of 2,2,4-trimethylpentane and isopropyl alcohol). The mixture was shaken for 15 minutes and stored overnight at room temperature, protected from light. The next morning 1 milliliter of water was added to the sample and shaken for 15 minutes. The sample was then centrifuged at approximately 1500 rpm for 15 minutes. Two ml of the organic phase (top layer) was transferred to a glass vial, dried at 37° C., under nitrogen, for approximately 1 hour, and then lyophilized for approximately 48 hours. The samples were then removed from the lyophilizer and each vial was reconstituted with 600 µl of solvent A (trimethylpentane/tetrahydrofuran (99:1). The samples were then recapped and vortexed for 5 minutes.

200 µl of each sample was then transferred to a pre-labeled 200 µl HPLC vial with 200 µL glass inserts. The HPLC vials were placed in the autosampler tray for the Agilent 1100 series HPLC unit. The Agilent 1100 HPLC system consisted of a thermostated autosampler, a quarternary pump, a column heater, and an A/D interface module. All components were controlled by Agilent ChemStation software. A Waters Spherisorb S3W 4.6×100 mm analytical column was maintained at 30° C. by the Agilent column heater unit. The HPLC autosampler was programmed to maintain the sample temperature at 20 C. throughout the run.

10 uL of each sample was injected in triplicate into the column. Two solvents were used for the solvent gradient. Solvent A was an admixture of trimethylpentane and tetrahydrofuran (99:1). Solvent B was ethylacetate. The gradient utilized is described in the table below:

| Time (min) | Solv A (%) | Solv B (%) | Flow (mL/min) |
|---|---|---|---|
| 0 | 99 | 1 | 2 |
| 2 | 96 | 4 | 2 |
| 6 | 60 | 40 | 2 |
| 7 | 5 | 95 | 2 |
| 10 | 5 | 95 | 2 |
| 10.1 | 99 | 1 | 2 |

The Sedex 75 Evaporative Light Scattering Detector (ELSD) was operated at 45° C. with a gain of 5, and $N_2$ pressure maintained at 3.1 bar. Analog signal obtained by the instrument was sent to the Agilent A/D interface module where it was converted to a digital output. The conversion was based on a 10000 mAU/volt set point and the data rate was set at 10 Hz (0.03 min). The resulting digital output was then feed into the Agilent ChemStation software for integration of the peak area.

The results of the HPLC analysis are reported below in Table IV. The results are reported as the reduction in cholesterol ester (CE) and wax ester (WE) production, when compared to the vehicle control. A negative value reflects an increase in sebum, whereas a positive reflects a decrease.

| Example # | % CE reduction | % WE reduction | Sum of WE & CE |
|---|---|---|---|
| 14 | 84 | 95 | 179 |
| 72 | 68 | 85 | 153 |

Example 78

Animal Model for Androgenetic Alopeica

As described above, alopecia is a problem that medical science has devoted considerable resources to. As with any disease process, animal models have been developed to allow scientists to screen compounds for their potential relative efficacy. Those compounds showing the greatest efficacy in these animal models are considered for further study in humans. Two different animal models have been developed to date for alopecia. The first is the telogen conversion assay, which uses female C3H/HeN mice. The second model uses stump-tailed macaques, which are monkeys that suffer from androgenetic alopecia.

The telogen conversion assay measures the potential of a compound to convert the resting stage of the hair growth cycle ("telogen") to the active stage of the hair growth cycle ("anagen") in mice. This assay takes advantage of the fact that the fur (i.e. hair) of 7-week-old C3H/HeN mice is in the telogen phase. This phase continues until about 75 days of age. In this assay, selected areas of the mice are shaved, contacted with a test agent, or a control, and the difference in the rate of hair growth is measured (i.e. induction of the anagen phase). The first sign of anagen is the darkening of skin color as melanocytes in the follicles start to synthesize melanin, in preparation for the production of pigmented hairs. This model has a number of advantages. This includes the ready availability of female CH3HeN mice, the ability to screen large numbers of compounds quickly, and the ease of housing and handling such animals.

The primary disadvantage of this model is its lack of androgenetic dependency. While the exact cause of human baldness is not known, it is well documented that androgens induce a regression of hair follicles in the scalp. This post adolescent regressive change is a fundamental cause of male pattern baldness, (i.e. "androgenetic alopecia). This phenomenon occurs in both men and women who have inherited the genetic trait for alopecia, as mentioned previously. For a more detail discussion of the effects of androgens on human scalps, the readers attention is directed to Trueb, R M, Molecular Mechanisms of Androgenic Alopecia, *Exp. Gerontology*, 2002, 27:981-990.

Researchers looked for other animals whose hair growth was similar to that of humans. These lead researchers to stump-tailed macaques. These primates also suffer from androgenetic alopecia. Essentially all post adolescent macaques, in both sexes, exhibit the development of baldness. Like the development of male pattern baldness in humans, androgens are an indispensable triggering factor in macaque baldness. Thinning of the frontal scalp hairs begins to appear around the same age (4 years) when serum levels of testosterone become drastically elevated in male animals. Although the elevation of testosterone in females is approximately one tenth that of the male level, there is no difference in the incidence and the age of onset of baldness between male and female stump-tailed macaques. Topical application of antiandrogens have reversed this baldness in animals of both sexes (Pan, H J et al, Evaluation of RU58841 as an antiandrogen in prostate PC3 cells and a topical anti-alopecia agent in the bald scalp of stump tailed macaques. *Endocrine* 1998; 9:39-43).

While this model is a significant improvement over the telogen conversion assay as a model for human baldness, it suffers from a number of practical disadvantages. The macaques are expensive, relatively rare, labor intensive to maintain, and require long wash out periods between testing. Thus, the macaque is not a practical model for screening large numbers of compounds It has been discovered that male C3H/HeN mice may be used in the telogen conversion assay, when evaluating anti-androgen test compounds. Thus, the model relates to a modification of the existing telogen conversion assay. Male C3H/HeN mice approximately 7 weeks old are utilized. These animals are also uniformly in telogen, like their female counterparts. However, once shaven, the androgens inherently present in these male mice inhibit the conversion of the hair follicles to the anagen phase. An anti-androgen will block this androgenic effect and the follicles will convert to anagen, like their female counterparts.

Example 78A

The compound described in Example 8 was submitted for further testing utilizing the modified telogen conversion assay, described above. The testing was carried out in the following manner.

Male C3H/HeN mice, 6 to 7 weeks old (Charles River Laboratories, Raleigh, N.C.) were used for the study. Fur was clipped from the dorsal region of the mice prior to initiation of the study. Only mice with pink skin, a visual indication of the telogen phase, were selected for inclusion in the study.

The test compound was dissolved in a vehicle consisting of propylene glycol (30%) and ethanol (70%) to achieve concentrations of 1% and 3% w/v. The relevant dose was applied topically to the clipped dorsal region of the mice in one test group (7-10 mice) in a volume of 20 µl/cm². A third group of animals received only the vehicle to serve as a control. Treatments were applied twice daily for 4 weeks.

The treatment area was observed and graded every other day for signs of hair growth. The hair growth response was quantified by recording, for each animal, the day on which signs of hair growth first appeared over the treated area. The first sign of anagen was the darkening of skin color as melanocytes in the follicles started to synthesize melanin in preparation for the production of pigmented hairs. The mice were observed for 35 days or longer.

Anagen was not initiated in either of the test groups prior to its occurrence in the vehicle control group.

Example 78B

The compound described in Example 72 was submitted for further testing utilizing the modified telogen conversion assay, described above. The testing was carried out in the following manner.

Male C3H/HeN mice, 6 to 7 weeks old (Charles River Laboratories, Raleigh, N.C.) were used for the study. Fur was clipped from the dorsal region of the mice prior to initiation of the study. Only mice with pink skin, a visual indication of the telogen phase, were selected for inclusion in the study.

The test compound was dissolved in a vehicle consisting of propylene glycol (30%) and ethanol (70%) to achieve a concentrations of 3% w/v. The relevant dose was applied topically to the clipped dorsal region of the mice in one test group (7-10 mice) in a volume of 20 µl/cm². A group of animals received only the vehicle to serve as a control. Treatments were applied twice daily for 4 weeks.

The treatment area was observed and graded every other day for signs of hair growth. The hair growth response was quantified by recording, for each animal, the day on which signs of hair growth first appeared over the treated area. The first sign of anagen was the darkening of skin color as melanocytes in the follicles started to synthesize melanin in preparation for the production of pigmented hairs. The mice were observed for 35 days or longer.

What is claimed is:

1. 4-(2-Cyano-cyclohexyloxy)-2-trifluoromethyl-benzonitrlle, a salt thereof, or an isomer thereof.

2. (trans)-(−)-4-(2-Cyano-cyclohexyloxy)-2-trifluoromethyl-benzonitrlle, or a pharmaceutically acceptable salt thereof.

3. A pharmaceutical composition comprising a compound according to claim 2 in admixture with one, or more, pharmaceutically acceptable excipients.

4. A kit comprising a compound according to claim 2, packaged for retail distribution, which advises a consumer how to utilize the compound to alleviate a condition selected from the group consisting of acne, alopecia, and oily skin.

5. A method for alleviating alopecia comprising the topical administration of an effective amount of a compound according to claim 2 to a human in need thereof.

6. A method for decreasing sebum secretion comprising the topical administration of an effective amount of compound according to claim 2 to a human in need thereof.

7. A topical formulation comprising a compound according to claim 2 in admixture with a dermatologically acceptable carrier.

8. A method for treating dermal disorders associated with excess sebum comprising the topical administration of an effective amount of a compound according to claim 2 to a patient in need thereof.

9. A method according to claim 8 in which said disorder is acne.

10. A method according to claim 8 in which said disorder is oily skin.

11. (trans)-(−)-4-(2-Cyano-cyclohexyloxy)-2-trifluoromethyl-benzonitrile, or a salt thereof.

12. 4-(2-Cyano-cyclohexyloxy)-2-trifluoromethyl-berizonitrile, or a pharmaceutically acceptable salt thereof.

* * * * *